US007855065B2

(12) United States Patent
Endo et al.

(10) Patent No.: US 7,855,065 B2
(45) Date of Patent: Dec. 21, 2010

(54) **MUTANT BACTERIUM BELONGING TO THE GENUS *BACILLUS***

(75) Inventors: Keiji Endo, Haga-gun (JP); Katsuya Ozaki, Haga-gun (JP)

(73) Assignee: Kao Corporation, Tokyo (JP)

( * ) Notice: Subject to any disclaimer, the term of this patent is extended or adjusted under 35 U.S.C. 154(b) by 1147 days.

(21) Appl. No.: 10/590,275

(22) PCT Filed: Mar. 4, 2005

(86) PCT No.: PCT/JP2005/003756

§ 371 (c)(1),
(2), (4) Date: Aug. 22, 2006

(87) PCT Pub. No.: WO2005/085437

PCT Pub. Date: Sep. 15, 2005

(65) Prior Publication Data

US 2009/0170154 A1     Jul. 2, 2009

(30) Foreign Application Priority Data

Mar. 5, 2004    (JP)   ............................. 2004-062852

(51) Int. Cl.
*C12N 1/20*     (2006.01)
*C12N 15/74*     (2006.01)
*C12N 15/75*     (2006.01)
*C12P 21/04*     (2006.01)

(52) U.S. Cl. ................. 435/252.31; 435/71.1; 435/471; 435/485

(58) Field of Classification Search ....................... None
See application file for complete search history.

(56) References Cited

FOREIGN PATENT DOCUMENTS

| EP | 1 065 277 A1 | 1/2001 |
| EP | 1 350 843 A2 | 10/2003 |
| JP | 6 327472 | 11/1994 |
| JP | 2000 184882 | 7/2000 |
| JP | 2000 210081 | 8/2000 |
| WO | 2003 054179 | 7/2003 |

OTHER PUBLICATIONS

Hengge-Aronis, Current Opinion in Microbiology, 2002, 5: pp. 591-595.*

Schnider, U. et al.,"Amplification of the housekeeping sigma factor in Pseudomonas flourescens CHAO enhances antibiotic production and improves biocontrol abilities", J. Bacteriol., vol. 177, No. 18. pp. 5387-5392, 1995.
Heldenwang, W. G. et al.," The sigma factors of *Bacillus subtilis*", Microbiol. Rev., vol. 59, No. 1, pp. 1-30, 1995.
Bird, T. et al.,"The effect of supercoiling on the in vitro transcription of the spoIIA operon from *Bacillus subtilis*", Biochimie, vol. 74, pp. 627-634, 1992.
Park, S.G. et al.,"Sequencing and phylogenetic analysis of the spoIIA operon from diverse *Bacillus and Paenibacillus* species", Gene, vol. 194, pp. 25-33, 1997.
Karen A. Hicks, et al., "Altering the level and regulation of the major sigma subunit of RNA polymerase affects gene expression and development in *Bacilus subtilis*", Molecular Microbiology, vol. 20, No. 1, XP002940914, 1996, pp. 201-212.
T. Kobayashi, et al. "Purification and Properties of an Alkaline Protease From *Alkalophilic Bacillus* sp. KSM-K16", Applied Microbiology and Biotechnology, XP-002434999, vol. 43, No. 3, Jul. 1995, 3 pages.
Office Action issued Sep. 14, 2010, in Japanese Application No. 2005-060483, filed Sep. 8, 2010 (with English-language Translation).
Qi, et al., "Localization of a Second SigH Promoter in the *Bacillus subtilis* sigA Operon and Regulation of dnaE Expresison by the Promoter", Journal of Bacteriology, vol. 172, No. 10, Oct. 1990, pp. 5631-5636.

* cited by examiner

*Primary Examiner*—Suzanne M Noakes
*Assistant Examiner*—Jae W Lee
(74) *Attorney, Agent, or Firm*—Oblon, Spivak, McClelland, Maier & Neustadt, L.L.P.

(57) ABSTRACT

The present invention provides a mutant *Bacillus* bacterium capable of enhancing productivity of proteins or polypeptides, a recombinant microorganism produced by introducing genes encoding heterologous proteins or polypeptides into the mutant *Bacillus* bacterium, and a method for producing proteins or polypeptides by use of the recombinant microorganism. A mutant *Bacillus* bacterium which has, on the genome or plasmid thereof, DNA having a promoter sequence which is recognized and transcribed specifically during the sporulation stage and which is ligated to an upstream end of a sigA gene or a gene equivalent thereto, a recombinant microorganism produced by introducing genes encoding heterologous proteins or polypeptides into the mutant *Bacillus* bacterium, and a method for producing proteins or polypeptides by use of the recombinant microorganism.

20 Claims, 2 Drawing Sheets

SEQUENCE LISTING

<160> NUMBER OF SEQ ID NOS: 28

<210> SEQ ID NO 1
<211> LENGTH: 371
<212> TYPE: PRT
<213> ORGANISM: Bacillus subtilis

<400> SEQUENCE: 1

Met Ala Asp Lys Gln Thr His Glu Thr Glu Leu Thr Phe Asp Gln Val
1               5                   10                  15

Lys Glu Gln Leu Thr Glu Ser Gly Lys Lys Arg Gly Val Leu Thr Tyr
                20                  25                  30

Glu Glu Ile Ala Glu Arg Met Ser Ser Phe Glu Ile Glu Ser Asp Gln
            35                  40                  45

Met Asp Glu Tyr Tyr Glu Phe Leu Gly Glu Gln Gly Val Glu Leu Ile
        50                  55                  60

Ser Glu Asn Glu Glu Thr Glu Asp Pro Asn Ile Gln Gln Leu Ala Lys
65                  70                  75                  80

Ala Glu Glu Glu Phe Asp Leu Asn Asp Leu Ser Val Pro Pro Gly Val
                85                  90                  95

Lys Ile Asn Asp Pro Val Arg Met Tyr Leu Lys Glu Ile Gly Arg Val
                100                 105                 110

Asn Leu Leu Ser Ala Lys Glu Glu Ile Ala Tyr Ala Gln Lys Ile Glu
            115                 120                 125

Glu Gly Asp Glu Glu Ser Lys Arg Arg Leu Ala Glu Ala Asn Leu Arg
        130                 135                 140

Leu Val Val Ser Ile Ala Lys Arg Tyr Val Gly Arg Gly Met Leu Phe
145                 150                 155                 160

Leu Asp Leu Ile His Glu Gly Asn Met Gly Leu Met Lys Ala Val Glu
              165                 170                 175

Lys Phe Asp Tyr Arg Lys Gly Tyr Lys Phe Ser Thr Tyr Ala Thr Trp
            180                 185                 190

Trp Ile Arg Gln Ala Ile Thr Arg Ala Ile Ala Asp Gln Ala Arg Thr
        195                 200                 205

Ile Arg Ile Pro Val His Met Val Glu Thr Ile Asn Lys Leu Ile Arg
    210                 215                 220

Val Gln Arg Gln Leu Leu Gln Asp Leu Gly Arg Glu Pro Thr Pro Glu
225                 230                 235                 240

Glu Ile Ala Glu Asp Met Asp Leu Thr Pro Glu Lys Val Arg Glu Ile
              245                 250                 255

Leu Lys Ile Ala Gln Glu Pro Val Ser Leu Glu Thr Pro Ile Gly Glu
            260                 265                 270

Glu Asp Asp Ser His Leu Gly Asp Phe Ile Glu Asp Gln Glu Ala Thr
        275                 280                 285

Ser Pro Ser Asp His Ala Ala Tyr Glu Leu Leu Lys Glu Gln Leu Glu
    290                 295                 300

Asp Val Leu Asp Thr Leu Thr Asp Arg Glu Glu Asn Val Leu Arg Leu
305                 310                 315                 320

Arg Phe Gly Leu Asp Asp Gly Arg Thr Arg Thr Leu Glu Glu Val Gly
              325                 330                 335

Lys Val Phe Gly Val Thr Arg Glu Arg Ile Arg Gln Ile Glu Ala Lys
            340                 345                 350

Ala Leu Arg Lys Leu Arg His Pro Ser Arg Ser Lys Arg Leu Lys Asp
        355                 360                 365

Phe Leu Glu
    370

<210> SEQ ID NO 2
<211> LENGTH: 1047
<212> TYPE: DNA
<213> ORGANISM: Bacillus subtilis

<400> SEQUENCE: 2
acagcctttc ttcctcattc tggacgagct tgaagaccct cataatcttg gttccattat      60
gaggacagca gatgcggtcg gcgctcatgg catcgtcatt ccaaaacgga gagctgtcgg     120
gctgacaaca cagtggcaa aagcttcaac aggagcaatt gagcacattc ctgtagcaag     180
agtcaccaat ttggcacgga cgttagaaga gatgaaagag cggggaatct gggttgtcgg     240
aacggatgcg tccgcgcgtg aggatttccg taatatggac ggcaatatgc ctttggctct     300
agtcatcgga agtgaaggaa agggatggg ccgccttgtg aaggaaaagt gcgattttct     360
cattaaactc ccgatggccg gaaaggtaac ttcactaaat gcatctgtcg cggctggtct     420
tttgatgtat gaagtctacc ggaaacgaaa ccctgtggga gaataaagac ccatggatat     480
cctgttagta gacgggtaca acatgattgg agcctggccg cagctgaagg atttaaaagc     540
gaacagtttt gaagaggcga gagacgtact gattcagaaa atggcggaat atcaatcgta     600
tacaggaaac agggttattg ttgttttgta cgcgcatctc gtaaagggc ttgagaaaaa     660 acagaccaac catagagttg aagtaatttt tacaaaagaa aatgacacgg ctgatgagcg     720
gatagaaaag ctcgctcagg ctttgaataa tattgcgact caaattcacg ttgcgacctc     780
tgactatact gagcagtggg cgattttcgg acagggggca ttgcgaaaat cggcccggga     840
gcttctgaga gaggtagaaa cgattgaaag gcgaatagag agacgggtaa gaaaaatcac     900

-continued

```
ttccgaaaag ccggcgggta aaattgcttt atcggaagag gttttgaaaa cgtttgaaaa      960
gtggaggcgg ggagacttag attaagttga cgcttttttg cccaatactg tataatattt     1020
ctatctacgt gcgccggggg gatcgga                                         1047
```

<210> SEQ ID NO 3
<211> LENGTH: 1143
<212> TYPE: DNA
<213> ORGANISM: Bacillus subtilis

<400> SEQUENCE: 3

```
gctgatagaa cgtgacacgg gaaaagtgct ttacaacaag aacagcaatg agagactggc       60
gcctgcaagc atgacgaaaa ttatgacgat gcttttgatt atggaagctt tagataaagg      120
caaaatcaaa atgagtgata aggtccgtac aagcgagcat gcggcgtcaa tgggcggctc      180
acagatattc cttgagcccg gcgaagaaat gactgtcaaa gaaatgctga aaggcatcgc      240
aatcgcttcg ggaaatgacg cttccgtcgc catggctgaa tttatttccg gctctgaaga      300
agaatttgtg aagaaaatga ataaaaaagc aaaagagctg ggattgaaaa atacatcctt      360
taaaaaccca acaggactga ccgaggaagg acactacagc tctgcttatg acatggcaat      420
catggctaag gaattattga aatacgaatc aattacgaag tttaccggca cgtatgaaga      480
ttatctgcgt gaaaatacag ataaaaagtt ttggcttgta aatacaaatc gccttatcaa      540
attttatcct ggtgtagacg gcgtaaaaac aggctataca ggcgaagcga atattgtct       600 gactgcttcg gctaaaaaag gaaacatgcg ggccatagcg gttgtattcg gagcgagcac      660
gcctaaagaa agaaacgcgc aagtgacaaa aatgcttgac ttcgcccttta gccaatatga      720 aacgcatcct ttatataaac gaaatcaaac agtagcaaaa gtaaaggtca aaaaggggaa      780
acaaaaattt atcgaactca ctacatctga gccgatttca atattgacga aaaaaggcga      840
ggatatgaac gatgtgaaaa aagaaatcaa gatgaaggac aatattagtg ctccgattca      900
aaaaggccaa gagcttggca ctcttgttct gaaaaaggat ggagaagtac tcgctgaaag      960
tcctgttgct gcaaaagaag atatgaagaa agccgggttt atcacattct aaagcggac     1020 gatgggagac tggacaaaat ttaagtaatt atgccgaatg accactagtt ttgtcacggt     1080
gaaggaattc attccgtcga aatcgaaaca ctcattatcc gatcatatca aggaggaatg     1140
agc                                                                   1143
```

<210> SEQ ID NO 4
<211> LENGTH: 795
<212> TYPE: PRT
<213> ORGANISM: Bacillus sp. KSM-S237

<400> SEQUENCE: 4

```
Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ser Asn Asp Trp Asp Ser Asn Met
65                  70                  75                  80

Ile Arg Leu Ala Met Tyr Val Gly Glu Asn Gly Tyr Ala Thr Asn Pro
```

```
                    85                  90                  95
Glu Leu Ile Lys Gln Arg Val Ile Asp Gly Ile Glu Leu Ala Ile Glu
                100                 105                 110

Asn Asp Met Tyr Val Ile Val Asp Trp His Val His Ala Pro Gly Asp
            115                 120                 125

Pro Arg Asp Pro Val Tyr Ala Gly Ala Lys Asp Phe Phe Arg Glu Ile
        130                 135                 140

Ala Ala Leu Tyr Pro Asn Asn Pro His Ile Ile Tyr Glu Leu Ala Asn
145                 150                 155                 160

Glu Pro Ser Ser Asn Asn Gly Gly Ala Gly Ile Pro Asn Asn Glu
                165                 170                 175

Glu Gly Trp Lys Ala Val Lys Glu Tyr Ala Asp Pro Ile Val Glu Met
                180                 185                 190

Leu Arg Lys Ser Gly Asn Ala Asp Asp Asn Ile Ile Ile Val Gly Ser
            195                 200                 205

Pro Asn Trp Ser Gln Arg Pro Asp Leu Ala Ala Asp Asn Pro Ile Asp
        210                 215                 220

Asp His His Thr Met Tyr Thr Val His Phe Tyr Thr Gly Ser His Ala
225                 230                 235                 240

Ala Ser Thr Glu Ser Tyr Pro Ser Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Ser Gly Asp Gly Gly Pro
        275                 280                 285

Tyr Phe Asp Glu Ala Asp Val Trp Ile Glu Phe Leu Asn Glu Asn Asn
290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335

Pro Gly Pro Asp His Val Trp Ala Pro Glu Glu Leu Ser Leu Ser Gly
            340                 345                 350

Glu Tyr Val Arg Ala Arg Ile Lys Gly Val Asn Tyr Glu Pro Ile Asp
        355                 360                 365

Arg Thr Lys Tyr Thr Lys Val Leu Trp Asp Phe Asn Asp Gly Thr Lys
370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
            420                 425                 430

Asn Gly Trp Gly Lys Ser Val Asp Ile Leu Gly Ala Glu Lys Leu Thr
        435                 440                 445

Met Asp Val Ile Val Asp Glu Pro Thr Thr Val Ala Ile Ala Ala Ile
450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
            500                 505                 510
```

-continued

Phe His Glu Glu Asp Asn Asn Met Asn Asn Ile Ile Leu Phe Val Gly
                515                 520                 525

Thr Asp Ala Ala Asp Val Ile Tyr Leu Asp Asn Ile Lys Val Ile Gly
            530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

Gly Glu Ser Gly Val Lys Thr Ala Leu Thr Ile Glu Glu Ala Asn Gly
            580                 585                 590

Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
    610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Gly Ala Asn Gln Val Asn Gly Leu Tyr His Tyr
        675                 680                 685

Glu Val Lys Ile Asn Val Arg Asp Ile Thr Asn Ile Gln Asp Asp Thr
    690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
        755                 760                 765

Glu Glu Lys Glu Ala Val Lys Glu Lys Lys Glu Ala Lys Glu Glu
    770                 775                 780

Lys Lys Ala Val Lys Asn Glu Ala Lys Lys Lys
785                 790                 795

<210> SEQ ID NO 5
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..(3044)

<400> SEQUENCE: 5
gatttgccga tgcaacaggc ttatatttag aggaaatttc tttttaaatt gaatacggaa    60
taaaatcagg taaacaggtc ctgattttat tttttgagt tttttagaga actgaagatt    120
gaaataaaag tagaagacaa aggacataag aaaattgcat tagttttaat tatagaaaac    180 gccttttat aattatttat acctagaacg aaaatactgt ttcgaaagcg gtttactata    240

```
aaaccttata ttccggctct tttttaaaac aggggggtaaa aattcactct agtattctaa      300
tttcaacatg ctataataaa tttgtaagac gcaatatgca tctctttttt tacgatatat      360
gtaagcggtt aaccttgtgc tatatgccga tttaggaagg ggggtagatt gagtcaagta      420
gtaataatat agataactta taagttgttg agaagcagga gagcatctgg gttactcaca      480
agttttttta aaactttaac gaaagcactt tcggtaatgc ttatgaattt agctatttga      540
ttcaattact ttaaaaatat ttaggaggta at atg atg tta aga aag aaa aca       593
                                   Met Met Leu Arg Lys Lys Thr
                                                       -25 aag cag ttg att tct tcc att ctt att tta gtt tta ctt cta tct tta       641
Lys Gln Leu Ile Ser Ser Ile Leu Ile Leu Val Leu Leu Leu Ser Leu
        -20             -15                 -10 ttt ccg gca gct ctt gca gca gaa gga aac act cgt gaa gac aat ttt       689
Phe Pro Ala Ala Leu Ala Ala Glu Gly Asn Thr Arg Glu Asp Asn Phe
 -5              -1   1               5                       10 aaa cat tta tta ggt aat gac aat gtt aaa cgc cct tct gag gct ggc       737
Lys His Leu Leu Gly Asn Asp Asn Val Lys Arg Pro Ser Glu Ala Gly
                 15                  20                  25 gca tta caa tta caa gaa gtc gat gga caa atg aca tta gta gat caa       785
Ala Leu Gln Leu Gln Glu Val Asp Gly Gln Met Thr Leu Val Asp Gln
         30                  35                  40 cat gga gaa aaa att caa tta cgt gga atg agt aca cac gga tta cag       833
His Gly Glu Lys Ile Gln Leu Arg Gly Met Ser Thr His Gly Leu Gln
         45                  50                  55 tgg ttt cct gag atc ttg aat gat aac gca tac aaa gct ctt tct aac       881
Trp Phe Pro Glu Ile Leu Asn Asp Asn Ala Tyr Lys Ala Leu Ser Asn
     60                  65                  70 gat tgg gat tcc aat atg att cgt ctt gct atg tat gta ggt gaa aat       929
Asp Trp Asp Ser Asn Met Ile Arg Leu Ala Met Tyr Val Gly Glu Asn
 75                  80                  85                  90 ggg tac gct aca aac cct gag tta atc aaa caa aga gtg att gat gga       977
Gly Tyr Ala Thr Asn Pro Glu Leu Ile Lys Gln Arg Val Ile Asp Gly
                 95                 100                 105 att gag tta gcg att gaa aat gac atg tat gtt att gtt gac tgg cat      1025
Ile Glu Leu Ala Ile Glu Asn Asp Met Tyr Val Ile Val Asp Trp His
             110                 115                 120 gtt cat gcg cca ggt gat cct aga gat cct gtt tat gca ggt gct aaa      1073
Val His Ala Pro Gly Asp Pro Arg Asp Pro Val Tyr Ala Gly Ala Lys
             125                 130                 135 gat ttc ttt aga gaa att gca gct tta tac cct aat aat cca cac att      1121
Asp Phe Phe Arg Glu Ile Ala Ala Leu Tyr Pro Asn Asn Pro His Ile
             140                 145                 150 att tat gag tta gcg aat gag ccg agt agt aat aat aat ggt gga gca      1169
Ile Tyr Glu Leu Ala Asn Glu Pro Ser Ser Asn Asn Asn Gly Gly Ala
155                 160                 165                 170 ggg att ccg aat aac gaa gaa ggt tgg aaa gcg gta aaa gaa tat gct      1217
Gly Ile Pro Asn Asn Glu Glu Gly Trp Lys Ala Val Lys Glu Tyr Ala
                 175                 180                 185 gat cca att gta gaa atg tta cgt aaa agc ggt aat gca gat gac aac      1265
Asp Pro Ile Val Glu Met Leu Arg Lys Ser Gly Asn Ala Asp Asp Asn
             190                 195                 200 att atc att gtt ggt agt cca aac tgg agt cag cgt ccg gac tta gca      1313
Ile Ile Ile Val Gly Ser Pro Asn Trp Ser Gln Arg Pro Asp Leu Ala
             205                 210                 215 gct gat aat cca att gat gat cac cat aca atg tat act gtt cac ttc      1361
Ala Asp Asn Pro Ile Asp Asp His His Thr Met Tyr Thr Val His Phe
             220                 225                 230
```

```
tac act ggt tca cat gct gct tca act gaa agc tat ccg tct gaa act    1409
Tyr Thr Gly Ser His Ala Ala Ser Thr Glu Ser Tyr Pro Ser Glu Thr
235                 240                 245                 250 cct aac tct gaa aga gga aac gta atg agt aac act cgt tat gcg tta    1457
Pro Asn Ser Glu Arg Gly Asn Val Met Ser Asn Thr Arg Tyr Ala Leu
                255                 260                 265 gaa aac gga gta gcg gta ttt gca aca gag tgg gga acg agt caa gct    1505
Glu Asn Gly Val Ala Val Phe Ala Thr Glu Trp Gly Thr Ser Gln Ala
270                 275                 280 agt gga gac ggt ggt cct tac ttt gat gaa gca gat gta tgg att gaa    1553
Ser Gly Asp Gly Gly Pro Tyr Phe Asp Glu Ala Asp Val Trp Ile Glu
            285                 290                 295 ttt tta aat gaa aac aac att agc tgg gct aac tgg tct tta acg aat    1601
Phe Leu Asn Glu Asn Asn Ile Ser Trp Ala Asn Trp Ser Leu Thr Asn
300                 305                 310 aaa aat gaa gta tct ggt gca ttt aca cca ttc gag tta ggt aag tct    1649
Lys Asn Glu Val Ser Gly Ala Phe Thr Pro Phe Glu Leu Gly Lys Ser
315                 320                 325                 330 aac gca acc aat ctt gac cca ggt cca gat cat gtg tgg gca cca gaa    1697
Asn Ala Thr Asn Leu Asp Pro Gly Pro Asp His Val Trp Ala Pro Glu
                335                 340                 345 gaa tta agt ctt tct gga gaa tat gta cgt gct cgt att aaa ggt gtg    1745
Glu Leu Ser Leu Ser Gly Glu Tyr Val Arg Ala Arg Ile Lys Gly Val
            350                 355                 360 aac tat gag cca atc gac cgt aca aaa tac acg aaa gta ctt tgg gac    1793
Asn Tyr Glu Pro Ile Asp Arg Thr Lys Tyr Thr Lys Val Leu Trp Asp
            365                 370                 375 ttt aat gat gga acg aag caa gga ttt gga gtg aat tcg gat tct cca    1841
Phe Asn Asp Gly Thr Lys Gln Gly Phe Gly Val Asn Ser Asp Ser Pro
380                 385                 390 aat aaa gaa ctt att gca gtt gat aat gaa aac aac act ttg aaa gtt    1889
Asn Lys Glu Leu Ile Ala Val Asp Asn Glu Asn Asn Thr Leu Lys Val
395                 400                 405                 410 tcg gga tta gat gta agt aac gat gtt tca gat ggc aac ttc tgg gct    1937
Ser Gly Leu Asp Val Ser Asn Asp Val Ser Asp Gly Asn Phe Trp Ala
                415                 420                 425 aat gct cgt ctt tct gcc aac ggt tgg gga aaa agt gtt gat att tta    1985
Asn Ala Arg Leu Ser Ala Asn Gly Trp Gly Lys Ser Val Asp Ile Leu
            430                 435                 440 ggt gct gag aag ctt aca atg gat gtt att gtt gat gaa cca acg acg    2033
Gly Ala Glu Lys Leu Thr Met Asp Val Ile Val Asp Glu Pro Thr Thr
            445                 450                 455 gta gct att gcg gcg att cca caa agt agt aaa agt gga tgg gca aat    2081
Val Ala Ile Ala Ala Ile Pro Gln Ser Ser Lys Ser Gly Trp Ala Asn
460                 465                 470 cca gag cgt gct gtt cga gtg aac gcg gaa gat ttt gtc cag caa acg    2129
Pro Glu Arg Ala Val Arg Val Asn Ala Glu Asp Phe Val Gln Gln Thr
475                 480                 485                 490 gac ggt aag tat aaa gct gga tta aca att aca gga gaa gat gct cct    2177
Asp Gly Lys Tyr Lys Ala Gly Leu Thr Ile Thr Gly Glu Asp Ala Pro
                495                 500                 505 aac cta aaa aat atc gct ttt cat gaa gaa gat aac aat atg aac aac    2225
Asn Leu Lys Asn Ile Ala Phe His Glu Glu Asp Asn Asn Met Asn Asn
            510                 515                 520 atc att ctg ttc gtg gga act gat gca gct gac gtt att tac tta gat    2273
Ile Ile Leu Phe Val Gly Thr Asp Ala Ala Asp Val Ile Tyr Leu Asp
            525                 530                 535 aac att aaa gta att gga aca gaa gtt gaa att cca gtt gtt cat gat    2321
Asn Ile Lys Val Ile Gly Thr Glu Val Glu Ile Pro Val Val His Asp
540                 545                 550
```

-continued

```
cca aaa gga gaa gct gtt ctt cct tct gtt ttt gaa gac ggt aca cgt        2369
Pro Lys Gly Glu Ala Val Leu Pro Ser Val Phe Glu Asp Gly Thr Arg
555                 560                 565                 570 caa ggt tgg gac tgg gct gga gag tct ggt gtg aaa aca gct tta aca        2417
Gln Gly Trp Asp Trp Ala Gly Glu Ser Gly Val Lys Thr Ala Leu Thr
            575                 580                 585 att gaa gaa gca aac ggt tct aac gcg tta tca tgg gaa ttt gga tat        2465
Ile Glu Glu Ala Asn Gly Ser Asn Ala Leu Ser Trp Glu Phe Gly Tyr
        590                 595                 600 cca gaa gta aaa cct agt gat aac tgg gca aca gct cca cgt tta gat        2513
Pro Glu Val Lys Pro Ser Asp Asn Trp Ala Thr Ala Pro Arg Leu Asp
    605                 610                 615 ttc tgg aaa tct gac ttg gtt cgc ggt gag aat gat tat gta gct ttt        2561
Phe Trp Lys Ser Asp Leu Val Arg Gly Glu Asn Asp Tyr Val Ala Phe
620                 625                 630 gat ttc tat cta gat cca gtt cgt gca aca gaa ggc gca atg aat atc        2609
Asp Phe Tyr Leu Asp Pro Val Arg Ala Thr Glu Gly Ala Met Asn Ile
635                 640                 645                 650 aat tta gta ttc cag cca cct act aac ggg tat tgg gta caa gca cca        2657
Asn Leu Val Phe Gln Pro Pro Thr Asn Gly Tyr Trp Val Gln Ala Pro
            655                 660                 665 aaa acg tat acg att aac ttt gat gaa tta gag gaa gcg aat caa gta        2705
Lys Thr Tyr Thr Ile Asn Phe Asp Glu Leu Glu Glu Ala Asn Gln Val
        670                 675                 680 aat ggt tta tat cac tat gaa gtg aaa att aac gta aga gat att aca        2753
Asn Gly Leu Tyr His Tyr Glu Val Lys Ile Asn Val Arg Asp Ile Thr
    685                 690                 695 aac att caa gat gac acg tta cta cgt aac atg atg atc att ttt gca        2801
Asn Ile Gln Asp Asp Thr Leu Leu Arg Asn Met Met Ile Ile Phe Ala
700                 705                 710 gat gta gaa agt gac ttt gca ggg aga gtc ttt gta gat aat gtt cgt        2849
Asp Val Glu Ser Asp Phe Ala Gly Arg Val Phe Val Asp Asn Val Arg
715                 720                 725                 730 ttt gag ggg gct gct act act gag ccg gtt gaa cca gag cca gtt gat        2897
Phe Glu Gly Ala Ala Thr Thr Glu Pro Val Glu Pro Glu Pro Val Asp
            735                 740                 745 cct ggc gaa gag acg cca cct gtc gat gag aag gaa gcg aaa aaa gaa        2945
Pro Gly Glu Glu Thr Pro Pro Val Asp Glu Lys Glu Ala Lys Lys Glu
        750                 755                 760 caa aaa gaa gca gag aaa gaa gag aaa gaa gca gta aaa gaa gaa aag        2993
Gln Lys Glu Ala Glu Lys Glu Glu Lys Glu Ala Val Lys Glu Glu Lys
    765                 770                 775 aaa gaa gct aaa gaa gaa aag aaa gca gtc aaa aat gag gct aag aaa        3041
Lys Glu Ala Lys Glu Glu Lys Lys Ala Val Lys Asn Glu Ala Lys Lys
780                 785                 790 aaa taatctatta aactagttat agggttatct aaaggtctga tgtagatctt             3094
Lys
795 ttagataacc tttttcttgc ataactggac acagagttgt tattaaagaa agtaag          3150

<210> SEQ ID NO 6
<211> LENGTH: 793
<212> TYPE: PRT
<213> ORGANISM: Bacillus sp. KSM-64

<400> SEQUENCE: 6

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
```

20                  25                  30
Val Asp Gly Gln Met Thr Leu Val Asp Gln His Gly Glu Lys Ile Gln
             35                  40                  45

Leu Arg Gly Met Ser Thr His Gly Leu Gln Trp Phe Pro Glu Ile Leu
         50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                 85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
            115                 120                 125

Pro Arg Asp Pro Val Tyr Ala Gly Ala Glu Asp Phe Phe Arg Asp Ile
            130                 135                 140

Ala Ala Leu Tyr Pro Asn Asn Pro His Ile Ile Tyr Glu Leu Ala Asn
145                 150                 155                 160

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
            195                 200                 205

Pro Asn Trp Ser Gln Arg Pro Asp Leu Ala Ala Asp Asn Pro Ile Asp
210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
            275                 280                 285

Tyr Phe Asp Glu Ala Asp Val Trp Ile Glu Phe Leu Asn Glu Asn Asn
            290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Ser Leu Asp
                325                 330                 335

Pro Gly Pro Asp Gln Val Trp Val Pro Glu Glu Leu Ser Leu Ser Gly
            340                 345                 350

Glu Tyr Val Arg Ala Arg Ile Lys Gly Val Asn Tyr Glu Pro Ile Asp
            355                 360                 365

Arg Thr Lys Tyr Thr Lys Val Leu Trp Asp Phe Asn Asp Gly Thr Lys
            370                 375                 380

Gln Gly Phe Gly Val Asn Gly Asp Ser Pro Val Glu Asp Val Val Ile
385                 390                 395                 400

Glu Asn Glu Ala Gly Ala Leu Lys Leu Ser Gly Leu Asp Ala Ser Asn
                405                 410                 415

Asp Val Ser Glu Gly Asn Tyr Trp Ala Asn Ala Arg Leu Ser Ala Asp
            420                 425                 430

Gly Trp Gly Lys Ser Val Asp Ile Leu Gly Ala Glu Lys Leu Thr Met
            435                 440                 445

```
Asp Val Ile Val Asp Glu Pro Thr Thr Val Ser Ile Ala Ala Ile Pro
    450                 455                 460

Gln Gly Pro Ser Ala Asn Trp Val Asn Pro Asn Arg Ala Ile Lys Val
465                 470                 475                 480

Glu Pro Thr Asn Phe Val Pro Leu Gly Asp Lys Phe Lys Ala Glu Leu
                    485                 490                 495

Thr Ile Thr Ser Ala Asp Ser Pro Ser Leu Glu Ala Ile Ala Met His
            500                 505                 510

Ala Glu Asn Asn Ile Asn Ile Ile Leu Phe Val Gly Thr Glu
        515                 520                 525

Gly Ala Asp Val Ile Tyr Leu Asp Asn Ile Lys Val Ile Gly Thr Glu
    530                 535                 540

Val Glu Ile Pro Val Val His Asp Pro Lys Gly Glu Ala Val Leu Pro
545                 550                 555                 560

Ser Val Phe Glu Asp Gly Thr Arg Gln Gly Trp Asp Trp Ala Gly Glu
                    565                 570                 575

Ser Gly Val Lys Thr Ala Leu Thr Ile Glu Glu Ala Asn Gly Ser Asn
            580                 585                 590

Ala Leu Ser Trp Glu Phe Gly Tyr Pro Glu Val Lys Pro Ser Asp Asn
        595                 600                 605

Trp Ala Thr Ala Pro Arg Leu Asp Phe Trp Lys Ser Asp Leu Val Arg
    610                 615                 620

Gly Glu Asn Asp Tyr Val Thr Phe Asp Phe Tyr Leu Asp Pro Val Arg
625                 630                 635                 640

Ala Thr Glu Gly Ala Met Asn Ile Asn Leu Val Phe Gln Pro Pro Thr
                    645                 650                 655

Asn Gly Tyr Trp Val Gln Ala Pro Lys Thr Tyr Thr Ile Asn Phe Asp
            660                 665                 670

Glu Leu Glu Glu Ala Asn Gln Val Asn Gly Leu Tyr His Tyr Glu Val
        675                 680                 685

Lys Ile Asn Val Arg Asp Ile Thr Asn Ile Gln Asp Asp Thr Leu Leu
    690                 695                 700

Arg Asn Met Met Ile Ile Phe Ala Asp Val Glu Ser Asp Phe Ala Gly
705                 710                 715                 720

Arg Val Phe Val Asp Asn Val Arg Phe Glu Gly Ala Ala Thr Thr Glu
                    725                 730                 735

Pro Val Glu Pro Glu Pro Val Asp Pro Gly Glu Glu Thr Pro Pro Val
            740                 745                 750

Asp Glu Lys Glu Ala Lys Lys Glu Gln Lys Glu Ala Glu Lys Glu Glu
        755                 760                 765

Lys Glu Ala Val Lys Glu Glu Lys Lys Glu Ala Lys Glu Glu Lys Lys
    770                 775                 780

Ala Ile Lys Asn Glu Ala Thr Lys Lys
785                 790

<210> SEQ ID NO 7
<211> LENGTH: 3332
<212> TYPE: DNA
<213> ORGANISM: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
```

-continued

```
<221> NAME/KEY: mat_peptide
<222> LOCATION: (697)..(3075)

<400> SEQUENCE: 7
agtacttacc attttagagt caaaagatag aagccaagca ggatttgccg atgcaaccgg    60
cttatattta gagggaattt cttttttaaat tgaatacgga ataaaatcag gtaaacaggt   120
cctgatttta ttttttttgaa ttttttttgag aactaaagat tgaaatagaa gtagaagaca  180
acggacataa gaaaattgta ttagttttaa ttatagaaaa cgcttttcta taattattta   240
tacctagaac gaaaatactg tttcgaaagc ggtttactat aaaaccttat attccggctc   300 ttttttttaaa caggggtgga aaattcactc tagtattcta atttcaacat gctataataa   360
atttgtaaga cgcaatatac atctttttttt tatgatatttt gtaagcggtt aaccttgtgc  420
tatatgccga tttaggaagg gggtagattg agtcaagtag tcataattta gataacttat   480
aagttgttga gaagcaggag agaatctggg ttactcacaa gttttttaaa acattatcga   540
aagcactttc ggttatgctt atgaatttag ctatttgatt caattacttt aataatttta   600 ggaggtaat atg atg tta aga aag aaa aca aag cag ttg att tct tcc att     651
           Met Met Leu Arg Lys Lys Thr Lys Gln Leu Ile Ser Ser Ile
                   -25                 -20 ctt att tta gtt tta ctt cta tct tta ttt ccg aca gct ctt gca gca       699
Leu Ile Leu Val Leu Leu Leu Ser Leu Phe Pro Thr Ala Leu Ala Ala
-15                 -10                 -5                  -1  1 gaa gga aac act cgt gaa gac aat ttt aaa cat tta tta ggt aat gac       747
Glu Gly Asn Thr Arg Glu Asp Asn Phe Lys His Leu Leu Gly Asn Asp
                 5                  10                  15 aat gtt aaa cgc cct tct gag gct ggc gca tta caa tta caa gaa gtc       795
Asn Val Lys Arg Pro Ser Glu Ala Gly Ala Leu Gln Leu Gln Glu Val
         20                  25                  30 gat gga caa atg aca tta gta gat caa cat gga gaa aaa att caa tta       843
Asp Gly Gln Met Thr Leu Val Asp Gln His Gly Glu Lys Ile Gln Leu
     35                  40                  45 cgt gga atg agt aca cac gga tta caa tgg ttt cct gag atc ttg aat       891
Arg Gly Met Ser Thr His Gly Leu Gln Trp Phe Pro Glu Ile Leu Asn
50                  55                  60                  65 gat aac gca tac aaa gct ctt gct aac gat tgg gaa tca aat atg att       939
Asp Asn Ala Tyr Lys Ala Leu Ala Asn Asp Trp Glu Ser Asn Met Ile
                 70                  75                  80 cgt cta gct atg tat gtc ggt gaa aat ggc tat gct tca aat cca gag       987
Arg Leu Ala Met Tyr Val Gly Glu Asn Gly Tyr Ala Ser Asn Pro Glu
             85                  90                  95 tta att aaa agc aga gtc att aaa gga ata gat ctt gct att gaa aat      1035
Leu Ile Lys Ser Arg Val Ile Lys Gly Ile Asp Leu Ala Ile Glu Asn
        100                 105                 110 gac atg tat gtc atc gtt gat tgg cat gta cat gca cct ggt gat cct      1083
Asp Met Tyr Val Ile Val Asp Trp His Val His Ala Pro Gly Asp Pro
    115                 120                 125 aga gat ccc gtt tac gct gga gca gaa gat ttc ttt aga gat att gca      1131
Arg Asp Pro Val Tyr Ala Gly Ala Glu Asp Phe Phe Arg Asp Ile Ala
130                 135                 140                 145 gca tta tat cct aac aat cca cac att att tat gag tta gcg aat gag      1179
Ala Leu Tyr Pro Asn Asn Pro His Ile Ile Tyr Glu Leu Ala Asn Glu
                150                 155                 160 cca agt agt aac aat aat ggt gga gct ggg att cca aat aat gaa gaa      1227
Pro Ser Ser Asn Asn Asn Gly Gly Ala Gly Ile Pro Asn Asn Glu Glu
            165                 170                 175 ggt tgg aat gcg gta aaa gaa tac gct gat cca att gta gaa atg tta      1275
Gly Trp Asn Ala Val Lys Glu Tyr Ala Asp Pro Ile Val Glu Met Leu
```

-continued

```
                    180                     185                     190
cgt gat agc ggg aac gca gat gac aat att atc att gtg ggt agt cca      1323
Arg Asp Ser Gly Asn Ala Asp Asp Asn Ile Ile Ile Val Gly Ser Pro
    195                 200                 205 aac tgg agt cag cgt cct gac tta gca gct gat aat cca att gat gat      1371
Asn Trp Ser Gln Arg Pro Asp Leu Ala Ala Asp Asn Pro Ile Asp Asp
210                 215                 220                 225 cac cat aca atg tat act gtt cac ttc tac act ggt tca cat gct gct      1419
His His Thr Met Tyr Thr Val His Phe Tyr Thr Gly Ser His Ala Ala
                230                 235                 240 tca act gaa agc tat ccg cct gaa act cct aac tct gaa aga gga aac      1467
Ser Thr Glu Ser Tyr Pro Pro Glu Thr Pro Asn Ser Glu Arg Gly Asn
            245                 250                 255 gta atg agt aac act cgt tat gcg tta gaa aac gga gta gca gta ttt      1515
Val Met Ser Asn Thr Arg Tyr Ala Leu Glu Asn Gly Val Ala Val Phe
        260                 265                 270 gca aca gag tgg gga act agc caa gca aat gga gat ggt ggt cct tac      1563
Ala Thr Glu Trp Gly Thr Ser Gln Ala Asn Gly Asp Gly Gly Pro Tyr
    275                 280                 285 ttt gat gaa gca gat gta tgg att gag ttt tta aat gaa aac aac att      1611
Phe Asp Glu Ala Asp Val Trp Ile Glu Phe Leu Asn Glu Asn Asn Ile
290                 295                 300                 305 agc tgg gct aac tgg tct tta acg aat aaa aat gaa gta tct ggt gca      1659
Ser Trp Ala Asn Trp Ser Leu Thr Asn Lys Asn Glu Val Ser Gly Ala
                310                 315                 320 ttt aca cca ttc gag tta ggt aag tct aac gca aca agt ctt gac cca      1707
Phe Thr Pro Phe Glu Leu Gly Lys Ser Asn Ala Thr Ser Leu Asp Pro
            325                 330                 335 ggg cca gac caa gta tgg gta cca gaa gag tta agt ctt tct gga gaa      1755
Gly Pro Asp Gln Val Trp Val Pro Glu Glu Leu Ser Leu Ser Gly Glu
        340                 345                 350 tat gta cgt gct cgt att aaa ggt gtg aac tat gag cca atc gac cgt      1803
Tyr Val Arg Ala Arg Ile Lys Gly Val Asn Tyr Glu Pro Ile Asp Arg
    355                 360                 365 aca aaa tac acg aaa gta ctt tgg gac ttt aat gat gga acg aag caa      1851
Thr Lys Tyr Thr Lys Val Leu Trp Asp Phe Asn Asp Gly Thr Lys Gln
370                 375                 380                 385 gga ttt gga gtg aat gga gat tct cca gtt gaa gat gta gtt att gag      1899
Gly Phe Gly Val Asn Gly Asp Ser Pro Val Glu Asp Val Val Ile Glu
                390                 395                 400 aat gaa gcg ggc gct tta aaa ctt tca gga tta gat gca agt aat gat      1947
Asn Glu Ala Gly Ala Leu Lys Leu Ser Gly Leu Asp Ala Ser Asn Asp
            405                 410                 415 gtt tct gaa ggt aat tac tgg gct aat gct cgt ctt tct gcc gac ggt      1995
Val Ser Glu Gly Asn Tyr Trp Ala Asn Ala Arg Leu Ser Ala Asp Gly
        420                 425                 430 tgg gga aaa agt gtt gat att tta ggt gct gaa aaa ctt act atg gat      2043
Trp Gly Lys Ser Val Asp Ile Leu Gly Ala Glu Lys Leu Thr Met Asp
    435                 440                 445 gtg att gtt gat gag ccg acc acg gta tca att gct gca att cca caa      2091
Val Ile Val Asp Glu Pro Thr Thr Val Ser Ile Ala Ala Ile Pro Gln
450                 455                 460                 465 ggg cca tca gcc aat tgg gtt aat cca aat cgt gca att aag gtt gag      2139
Gly Pro Ser Ala Asn Trp Val Asn Pro Asn Arg Ala Ile Lys Val Glu
                470                 475                 480 cca act aat ttc gta ccg tta gga gat aag ttt aaa gcg gaa tta act      2187
Pro Thr Asn Phe Val Pro Leu Gly Asp Lys Phe Lys Ala Glu Leu Thr
            485                 490                 495 ata act tca gct gac tct cca tcg tta gaa gct att gcg atg cat gct      2235
Ile Thr Ser Ala Asp Ser Pro Ser Leu Glu Ala Ile Ala Met His Ala
```

```
                Ile Thr Ser Ala Asp Ser Pro Ser Leu Glu Ala Ile Ala Met His Ala
                                500                 505                 510 gaa aat aac aac atc aac aac atc att ctt ttt gta gga act gaa ggt         2283
Glu Asn Asn Asn Ile Asn Asn Ile Ile Leu Phe Val Gly Thr Glu Gly
515                 520                 525 gct gat gtt atc tat tta gat aac att aaa gta att gga aca gaa gtt         2331
Ala Asp Val Ile Tyr Leu Asp Asn Ile Lys Val Ile Gly Thr Glu Val
530                 535                 540                 545 gaa att cca gtt gtt cat gat cca aaa gga gaa gct gtt ctt cct tct         2379
Glu Ile Pro Val Val His Asp Pro Lys Gly Glu Ala Val Leu Pro Ser
                550                 555                 560 gtt ttt gaa gac ggt aca cgt caa ggt tgg gac tgg gct gga gag tct         2427
Val Phe Glu Asp Gly Thr Arg Gln Gly Trp Asp Trp Ala Gly Glu Ser
565                 570                 575 ggt gtg aaa aca gct tta aca att gaa gaa gca aac ggt tct aac gcg         2475
Gly Val Lys Thr Ala Leu Thr Ile Glu Glu Ala Asn Gly Ser Asn Ala
        580                 585                 590 tta tca tgg gaa ttt gga tac cca gaa gta aaa cct agt gat aac tgg         2523
Leu Ser Trp Glu Phe Gly Tyr Pro Glu Val Lys Pro Ser Asp Asn Trp
    595                 600                 605 gca aca gct cca cgt tta gat ttc tgg aaa tct gac ttg gtt cgc ggt         2571
Ala Thr Ala Pro Arg Leu Asp Phe Trp Lys Ser Asp Leu Val Arg Gly
610                 615                 620                 625 gaa aat gat tat gta act ttt gat ttc tat cta gat cca gtt cgt gca         2619
Glu Asn Asp Tyr Val Thr Phe Asp Phe Tyr Leu Asp Pro Val Arg Ala
                630                 635                 640 aca gaa ggc gca atg aat atc aat tta gta ttc cag cca cct act aac         2667
Thr Glu Gly Ala Met Asn Ile Asn Leu Val Phe Gln Pro Pro Thr Asn
            645                 650                 655 ggg tat tgg gta caa gca cca aaa acg tat acg att aac ttt gat gaa         2715
Gly Tyr Trp Val Gln Ala Pro Lys Thr Tyr Thr Ile Asn Phe Asp Glu
        660                 665                 670 tta gag gaa gcg aat caa gta aat ggt tta tat cac tat gaa gtg aaa         2763
Leu Glu Glu Ala Asn Gln Val Asn Gly Leu Tyr His Tyr Glu Val Lys
    675                 680                 685 att aac gta aga gat att aca aac att caa gat gac acg tta cta cgt         2811
Ile Asn Val Arg Asp Ile Thr Asn Ile Gln Asp Asp Thr Leu Leu Arg
690                 695                 700                 705 aac atg atg atc att ttt gca gat gta gaa agt gac ttt gca ggg aga         2859
Asn Met Met Ile Ile Phe Ala Asp Val Glu Ser Asp Phe Ala Gly Arg
                710                 715                 720 gtc ttt gta gat aat gtt cgt ttt gag ggg gct gct act act gag ccg         2907
Val Phe Val Asp Asn Val Arg Phe Glu Gly Ala Ala Thr Thr Glu Pro
            725                 730                 735 gtt gaa cca gag cca gtt gat cct ggc gaa gag acg ccg cct gtc gat         2955
Val Glu Pro Glu Pro Val Asp Pro Gly Glu Glu Thr Pro Pro Val Asp
        740                 745                 750 gag aag gaa gcg aaa aaa gaa caa aaa gaa gca gag aaa gaa gag aaa         3003
Glu Lys Glu Ala Lys Lys Glu Gln Lys Glu Ala Glu Lys Glu Glu Lys
    755                 760                 765 gaa gca gta aaa gaa gaa aag aaa gaa gct aaa gaa gaa aag aaa gca         3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct       3105
Ile Lys Asn Glu Ala Thr Lys Lys
                790 aaaggtctga tgcagatctt ttagataacc tttttttgca taactggaca tagaatggtt      3165 attaagaaa gcaaggtgtt tatacgatat taaaaggta gcgattttaa attgaaacct        3225
```

-continued

```
ttaataatgt cttgtgatag aatgatgaag taatttaaga gggggaaacg aagtgaaaac    3285
ggaaatttct agtagaagaa aaacagacca agaaatactg caagctt                  3332
```

<210> SEQ ID NO 8
<211> LENGTH: 20
<212> TYPE: DNA
<213> ORGANISM: artificial sequence
<220> FEATURE:
<223> OTHER INFORMATION: Oligonucleotide as PCR primer designed from
      nucleotide sequence of sigA in Bacillus subtilis

<400> SEQUENCE: 8

```
atggctgata aacaaaccca                                                  20
```

<210> SEQ ID NO 9
<211> LENGTH: 20
<212> TYPE: DNA
<213> ORGANISM: artificial sequence
<220> FEATURE:
<223> OTHER INFORMATION: Oligonucleotide as PCR primer designed from
      nucleotide sequence of sigA in Bacillus subtilis

<400> SEQUENCE: 9

```
caccacaatg ttcatttgca                                                  20
```

<210> SEQ ID NO 10
<211> LENGTH: 21
<212> TYPE: DNA
<213> ORGANISM: artificial sequence
<220> FEATURE:
<223> OTHER INFORMATION: Oligonucleotide as PCR primer designed from
      nucleotide sequence of the upstream region of sigH in Bacillus
      subtilis

<400> SEQUENCE: 10

```
acagcctttc ttcctcattc t                                                21
```

<210> SEQ ID NO 11
<211> LENGTH: 42
<212> TYPE: DNA
<213> ORGANISM: artificial sequence
<220> FEATURE:
<223> OTHER INFORMATION: Oligonucleotide as PCR primer; 3'-portion from
      nucleotide sequence of the upstream region of sigH in Bacillus
      subtilis; 5'-portion from nucleotide sequence of sigA in Bacillus
      subtilis

<400> SEQUENCE: 11

```
cgtgggtttg tttatcagcc attccgatcc ccccggcgca cg                         42
```

<210> SEQ ID NO 12
<211> LENGTH: 21
<212> TYPE: DNA
<213> ORGANISM: artificial sequence
<220> FEATURE:
<223> OTHER INFORMATION: Oligonucleotide as PCR primer designed from
      nucleotide sequence of the upstream region of sigF in Bacillus
      subtilis

<400> SEQUENCE: 12

```
gctgatagaa cgtgacacgg g                                                21
```

<210> SEQ ID NO 13
<211> LENGTH: 42
<212> TYPE: DNA
<213> ORGANISM: artificial sequence
<220> FEATURE:

-continued

<223> OTHER INFORMATION: Oligonucleotide as PCR primer; 3'-portion from
      the upstream region of sigF in Bacillus subtilis; 5'-portion from
      sigA in Bacillus subtilis

<400> SEQUENCE: 13
cgtgggtttg tttatcagcc atgctcattc ctccttgata tg                      42

<210> SEQ ID NO 14
<211> LENGTH: 19
<212> TYPE: DNA
<213> ORGANISM: artificial sequence
<220> FEATURE:
<223> OTHER INFORMATION: Oligonucleotide as PCR primer designed from
      nucleotide sequence of plasmid pC194

<400> SEQUENCE: 14
caactaaagc acccattag                                                19

<210> SEQ ID NO 15
<211> LENGTH: 44
<212> TYPE: DNA
<213> ORGANISM: artificial sequence
<220> FEATURE:
<223> OTHER INFORMATION: Oligonucleotide as PCR primer; its 3'-portion
      from plasmid pC194 and its 5'-portion from sigA in Bacillus
      subtilis

<400> SEQUENCE: 15
catttgcaaa tgaacattgt ggtgcttctt caactaacgg ggca                    44

<210> SEQ ID NO 16
<211> LENGTH: 20
<212> TYPE: DNA
<213> ORGANISM: artificial sequence
<220> FEATURE:
<223> OTHER INFORMATION: Oligonucleotide as PCR primer from nucleotide
      sequence of sigA in Bacillus subtilis; the sequence containing a
      nucleotide substitution for destroying the initiation codon of
      sigA

<400> SEQUENCE: 16
atagctgata aacaaaccca                                               20

<210> SEQ ID NO 17
<211> LENGTH: 42
<212> TYPE: DNA
<213> ORGANISM: artificial sequence
<220> FEATURE:
<223> OTHER INFORMATION: Oligonucleotide as PCR primer; 3'-portion from
      the upstream region of sigF and 5'-portion from sigA in Bacillus
      subtilis; the sequence containing a nucleotide substitution for
      destroying the initiation codon of sigA

<400> SEQUENCE: 17
cgtgggtttg tttatcagct atgctcattc ctccttgata tg                      42

<210> SEQ ID NO 18
<211> LENGTH: 1795
<212> TYPE: DNA
<213> ORGANISM: Bacillus sp. KSM-K38
<220> FEATURE:
<221> NAME/KEY: CDS
<222> LOCATION: (212)..(1714)
<220> FEATURE:
<221> NAME/KEY: sig_peptide
<222> LOCATION: (212)..(274)
<220> FEATURE:
<221> NAME/KEY: mat_peptide
<222> LOCATION: (275)..(1714)

<400> SEQUENCE: 18

```
caggccagcc aaagtagcca ccaactaagt aacatcgatt caggataaaa gtatgcgaaa      60
cgatgcgcaa aactgcgcaa ctactagcac tcttcaggga ctaaaccacc tttttttccaa    120 aaatgacatc atataaacaa atttgtctac caatcactat ttaaagctgt ttatgatata    180
tgtaagcgtt atcattaaaa ggaggtattt g atg aga aga tgg gta gta gca      232
                                   Met Arg Arg Trp Val Val Ala
                                       -20             -15 atg ttg gca gtg tta ttt tta ttt cct tcg gta gta gtt gca gat gga      280
Met Leu Ala Val Leu Phe Leu Phe Pro Ser Val Val Val Ala Asp Gly
            -10              -5               -1  1 ttg aac ggt acg atg atg cag tat tat gag tgg cat ttg gaa aac gac      328
Leu Asn Gly Thr Met Met Gln Tyr Tyr Glu Trp His Leu Glu Asn Asp
        5                10                  15 ggg cag cat tgg aat cgg ttg cac gat gat gcc gca gct ttg agt gat      376
Gly Gln His Trp Asn Arg Leu His Asp Asp Ala Ala Ala Leu Ser Asp
    20                  25                  30 gct ggt att aca gct att tgg att ccg cca gcc tac aaa ggt aat agt      424
Ala Gly Ile Thr Ala Ile Trp Ile Pro Pro Ala Tyr Lys Gly Asn Ser
35                  40                  45                  50 cag gcg gat gtt ggg tac ggt gca tac gat ctt tat gat tta gga gag      472
Gln Ala Asp Val Gly Tyr Gly Ala Tyr Asp Leu Tyr Asp Leu Gly Glu
                55                  60                  65 ttc aat caa aag ggt act gtt cga acg aaa tac gga act aag gca cag      520
Phe Asn Gln Lys Gly Thr Val Arg Thr Lys Tyr Gly Thr Lys Ala Gln
            70                  75                  80 ctt gaa cga gct att ggg tcc ctt aaa tct aat gat atc aat gta tac      568
Leu Glu Arg Ala Ile Gly Ser Leu Lys Ser Asn Asp Ile Asn Val Tyr
        85                  90                  95 gga gat gtc gtg atg aat cat aaa atg gga gct gat ttt acg gag gca      616
Gly Asp Val Val Met Asn His Lys Met Gly Ala Asp Phe Thr Glu Ala
    100                 105                 110 gtg caa gct gtt caa gta aat cca acg aat cgt tgg cag gat att tca      664
Val Gln Ala Val Gln Val Asn Pro Thr Asn Arg Trp Gln Asp Ile Ser
115                 120                 125                 130 ggt gcc tac acg att gat gcg tgg acg ggt ttc gac ttt tca ggg cgt      712
Gly Ala Tyr Thr Ile Asp Ala Trp Thr Gly Phe Asp Phe Ser Gly Arg
                135                 140                 145 aac aac gcc tat tca gat ttt aag tgg aga tgg ttc cat ttt aat ggt      760
Asn Asn Ala Tyr Ser Asp Phe Lys Trp Arg Trp Phe His Phe Asn Gly
            150                 155                 160 gtt gac tgg gat cag cgc tat caa gaa aat cat att ttc cgc ttt gca      808
Val Asp Trp Asp Gln Arg Tyr Gln Glu Asn His Ile Phe Arg Phe Ala
        165                 170                 175 aat acg aac tgg aac tgg cga gtg gat gaa gag aac ggt aat tat gat      856
Asn Thr Asn Trp Asn Trp Arg Val Asp Glu Glu Asn Gly Asn Tyr Asp
    180                 185                 190 tac ctg tta gga tcg aat atc gac ttt agt cat cca gaa gta caa gat      904
Tyr Leu Leu Gly Ser Asn Ile Asp Phe Ser His Pro Glu Val Gln Asp
195                 200                 205                 210 gag ttg aag gat tgg ggt agc tgg ttt acc gat gag tta gat ttg gat      952
Glu Leu Lys Asp Trp Gly Ser Trp Phe Thr Asp Glu Leu Asp Leu Asp
                215                 220                 225 ggt tat cgt tta gat gct att aaa cat att cca ttc tgg tat aca tct     1000
Gly Tyr Arg Leu Asp Ala Ile Lys His Ile Pro Phe Trp Tyr Thr Ser
            230                 235                 240 gat tgg gtt cgg cat cag cgc aac gaa gca gat caa gat tta ttt gtc     1048
Asp Trp Val Arg His Gln Arg Asn Glu Ala Asp Gln Asp Leu Phe Val
```

```
gta ggg gaa tat tgg aag gat gac gta ggt gct ctc gaa ttt tat tta      1096
Val Gly Glu Tyr Trp Lys Asp Asp Val Gly Ala Leu Glu Phe Tyr Leu
    260                 265                 270 gat gaa atg aat tgg gag atg tct cta ttc gat gtt cca ctt aat tat      1144
Asp Glu Met Asn Trp Glu Met Ser Leu Phe Asp Val Pro Leu Asn Tyr
275                 280                 285                 290 aat ttt tac cgg gct tca caa caa ggt gga agc tat gat atg cgt aat      1192
Asn Phe Tyr Arg Ala Ser Gln Gln Gly Gly Ser Tyr Asp Met Arg Asn
                295                 300                 305 att tta cga gga tct tta gta gaa gcg cat ccg atg cat gca gtt acg      1240
Ile Leu Arg Gly Ser Leu Val Glu Ala His Pro Met His Ala Val Thr
            310                 315                 320 ttt gtt gat aat cat gat act cag cca ggg gag tca tta gag tca tgg      1288
Phe Val Asp Asn His Asp Thr Gln Pro Gly Glu Ser Leu Glu Ser Trp
        325                 330                 335 gtt gct gat tgg ttt aag cca ctt gct tat gcg aca att ttg acg cgt      1336
Val Ala Asp Trp Phe Lys Pro Leu Ala Tyr Ala Thr Ile Leu Thr Arg
    340                 345                 350 gaa ggt ggt tat cca aat gta ttt tac ggt gat tac tat ggg att cct      1384
Glu Gly Gly Tyr Pro Asn Val Phe Tyr Gly Asp Tyr Tyr Gly Ile Pro
355                 360                 365                 370 aac gat aac att tca gct aaa aaa gat atg att gat gag ctg ctt gat      1432
Asn Asp Asn Ile Ser Ala Lys Lys Asp Met Ile Asp Glu Leu Leu Asp
                375                 380                 385 gca cgt caa aat tac gca tat ggc acg cag cat gac tat ttt gat cat      1480
Ala Arg Gln Asn Tyr Ala Tyr Gly Thr Gln His Asp Tyr Phe Asp His
            390                 395                 400 tgg gat gtt gta gga tgg act agg gaa gga tct tcc tcc aga cct aat      1528
Trp Asp Val Val Gly Trp Thr Arg Glu Gly Ser Ser Ser Arg Pro Asn
        405                 410                 415 tca ggc ctt gcg act att atg tcg aat gga cct ggt ggt tcc aag tgg      1576
Ser Gly Leu Ala Thr Ile Met Ser Asn Gly Pro Gly Gly Ser Lys Trp
    420                 425                 430 atg tat gta gga cgt cag aat gca gga caa aca tgg aca gat tta act      1624
Met Tyr Val Gly Arg Gln Asn Ala Gly Gln Thr Trp Thr Asp Leu Thr
435                 440                 445                 450 ggt aat aac gga gcg tcc gtt aca att aat ggc gat gga tgg ggc gaa      1672
Gly Asn Asn Gly Ala Ser Val Thr Ile Asn Gly Asp Gly Trp Gly Glu
                455                 460                 465 ttc ttt acg aat gga gga tct gta tcc gtg tac gtg aac caa taacaaaaa   1723
Phe Phe Thr Asn Gly Gly Ser Val Ser Val Tyr Val Asn Gln
            470                 475                 480 gccttgagaa gggattcctc cctaactcaa ggctttcttt atgtcgctta gctttacgct   1783
tctacgactt tg                                                         1795

<210> SEQ ID NO 19
<211> LENGTH: 480
<212> TYPE: PRT
<213> ORGANISM: Bacillus sp. KSM-K38

<400> SEQUENCE: 19

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45
```

-continued

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln

| | | | |
|---|---|---|---|
| 465 | 470 | 475 | 480 |

<210> SEQ ID NO 20
<211> LENGTH: 1441
<212> TYPE: DNA
<213> ORGANISM: Bacillus clausii KSM-K16
<220> FEATURE:
<221> NAME/KEY: CDS
<222> LOCATION: (164)..(1303)

<400> SEQUENCE: 20

```
tggtagcttt ccccacttga aaccgtttta atcaaaaaac aaagtgggaa aattctgtta      60
acttaatgtt aataattgtt tcccaatagg caaatctttc taactttgat acgtttaaac     120
taccagcttg acgagttgg gataaaagtg aggagggaac cga atg aag aaa ccg        175
                                             Met Lys Lys Pro
                                               1 ttg ggg aaa att gtc gca agc acc gca cta ctc att tct gtt gct ttt       223
Leu Gly Lys Ile Val Ala Ser Thr Ala Leu Leu Ile Ser Val Ala Phe
  5              10                  15                  20 agt tca tcg atc gca tcg gct gct gag gaa gca aaa gaa aaa tat tta       271
Ser Ser Ser Ile Ala Ser Ala Ala Glu Glu Ala Lys Glu Lys Tyr Leu
             25                  30                  35 att ggc ttt aat gag cag gaa gca gtt agt gag ttt gta gag caa ata       319
Ile Gly Phe Asn Glu Gln Glu Ala Val Ser Glu Phe Val Glu Gln Ile
         40                  45                  50 gag gca aat gac gat gtc gcg att ctc tct gag gaa gag gaa gtc gaa       367
Glu Ala Asn Asp Asp Val Ala Ile Leu Ser Glu Glu Glu Glu Val Glu
     55                  60                  65 att gaa ttg ctt cat gag ttt gaa acg att cct gtt tta tct gtt gag       415
Ile Glu Leu Leu His Glu Phe Glu Thr Ile Pro Val Leu Ser Val Glu
 70                  75                  80 tta agt cca gaa gat gtg gac gcg ctt gag ctc gat cca acg att tcg       463
Leu Ser Pro Glu Asp Val Asp Ala Leu Glu Leu Asp Pro Thr Ile Ser
 85                  90                  95                 100 tat att gaa gag gat gca gaa gta acg aca atg gcg caa tca gtg cca       511
Tyr Ile Glu Glu Asp Ala Glu Val Thr Thr Met Ala Gln Ser Val Pro
                105                 110                 115 tgg gga att agc cgt gta caa gcc cca gct gcc cat aac cgt gga ttg       559
Trp Gly Ile Ser Arg Val Gln Ala Pro Ala Ala His Asn Arg Gly Leu
            120                 125                 130 aca ggt tct ggt gta aaa gtt gct gtc ctc gat acg ggt att tcc acc       607
Thr Gly Ser Gly Val Lys Val Ala Val Leu Asp Thr Gly Ile Ser Thr
        135                 140                 145 cat cca gac tta aat att cgc ggt ggt gct agc ttt gtg cca gga gaa       655
His Pro Asp Leu Asn Ile Arg Gly Gly Ala Ser Phe Val Pro Gly Glu
    150                 155                 160 cca tcc act caa gat gga aat gga cat ggc acg cat gtg gca ggg acg       703
Pro Ser Thr Gln Asp Gly Asn Gly His Gly Thr His Val Ala Gly Thr
165                 170                 175                 180 att gct gct tta aac aat tcg att ggc gtt ctg ggc gta gca ccg agc       751
Ile Ala Ala Leu Asn Asn Ser Ile Gly Val Leu Gly Val Ala Pro Ser
                185                 190                 195 gcg gaa cta tac gct gta aaa gta tta ggc gcg agc ggt tca ggt tcg       799
Ala Glu Leu Tyr Ala Val Lys Val Leu Gly Ala Ser Gly Ser Gly Ser
            200                 205                 210 gtc agc tcg att gcc caa gga ttg gaa tgg gca ggg aac aat ggc atg       847
Val Ser Ser Ile Ala Gln Gly Leu Glu Trp Ala Gly Asn Asn Gly Met
        215                 220                 225 cac gtt gcg aat ttg agt tta gga agc ccg tcg ccg agt gca aca ctt       895
His Val Ala Asn Leu Ser Leu Gly Ser Pro Ser Pro Ser Ala Thr Leu
```

-continued

```
                230                 235                 240
gag caa gct gtt aat agc gct act tct aga ggc gtt ctt gtc gta gca    943
Glu Gln Ala Val Asn Ser Ala Thr Ser Arg Gly Val Leu Val Val Ala
245                 250                 255                 260 gca tct ggt aat tca ggt gca ggc tca atc agc tat ccg gcc cgt tat    991
Ala Ser Gly Asn Ser Gly Ala Gly Ser Ile Ser Tyr Pro Ala Arg Tyr
                265                 270                 275 gcg aac gca atg gca gtc gga gcg act gac caa aac aac aac cgc gct   1039
Ala Asn Ala Met Ala Val Gly Ala Thr Asp Gln Asn Asn Asn Arg Ala
            280                 285                 290 agc ttt tca cag tat gga gct ggg ctt gac att gtc gcg cca ggt gtc   1087
Ser Phe Ser Gln Tyr Gly Ala Gly Leu Asp Ile Val Ala Pro Gly Val
        295                 300                 305 aat gtg cag agc aca tac cca ggt tca aca tat gcc agc tta aac ggt   1135
Asn Val Gln Ser Thr Tyr Pro Gly Ser Thr Tyr Ala Ser Leu Asn Gly
    310                 315                 320 aca tcg atg gct act cct cat gtt gca ggt gta gca gcc ctt gtt aaa   1183
Thr Ser Met Ala Thr Pro His Val Ala Gly Val Ala Ala Leu Val Lys
325                 330                 335                 340 caa aag aat cca tct tgg tcc aat gta caa atc cgc aat cat cta aag   1231
Gln Lys Asn Pro Ser Trp Ser Asn Val Gln Ile Arg Asn His Leu Lys
                345                 350                 355 aat acg gca acg ggt tta gga aac acg aac ttg tat gga agc ggg ctt   1279
Asn Thr Ala Thr Gly Leu Gly Asn Thr Asn Leu Tyr Gly Ser Gly Leu
            360                 365                 370 gtc aat gca gaa gcg gca aca cgc taatcaataa taataacgct gtgtgcttta  1333
Val Asn Ala Glu Ala Ala Thr Arg
        375                 380 agcacacagc gttttttagt gtgtatgaat cgaaaaagag aaatagatcg ctgatttcaa  1393
aaagcgagcg taagggcta ttgaagctct ttacgcttgc aggatttg                1441

<210> SEQ ID NO 21
<211> LENGTH: 380
<212> TYPE: PRT
<213> ORGANISM: Bacillus clausii KSM-K16

<400> SEQUENCE: 21

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Ala Val Ser Glu Phe
        35                  40                  45

Val Glu Gln Ile Glu Ala Asn Asp Asp Val Ala Ile Leu Ser Glu Glu
50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
            85                  90                  95

Pro Thr Ile Ser Tyr Ile Glu Glu Asp Ala Glu Val Thr Thr Met Ala
        100                 105                 110

Gln Ser Val Pro Trp Gly Ile Ser Arg Val Gln Ala Pro Ala Ala His
    115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160
```

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Val Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Gly Leu Gly Asn Thr Asn Leu Tyr
        355                 360                 365

Gly Ser Gly Leu Val Asn Ala Glu Ala Ala Thr Arg
    370                 375                 380

<210> SEQ ID NO 22
<211> LENGTH: 46
<212> TYPE: DNA
<213> ORGANISM: Artificial
<220> FEATURE:
<223> OTHER INFORMATION: Oligonucleotide as PCR primer; 3'-portion from
      the alkaline protease gene in Bacillus clausii KSM-K16; 5'-portion
      from upstream region of alkaline cellulase gene in Bacillus sp.
      KSM-S237

<400> SEQUENCE: 22
actttaaaaa tatttaggag gtaatatgaa gaaaccgttg gggaaa                  46

<210> SEQ ID NO 23
<211> LENGTH: 32
<212> TYPE: DNA
<213> ORGANISM: Artificial
<220> FEATURE:
<223> OTHER INFORMATION: Oligonucleotide as PCR primer designed from the
      downstream region of the alkaline protease gene in Bacillus
      clausii KSM-K16 with a insertion of the BglII restriction site at
      the 5'-end

<400> SEQUENCE: 23
gggagatctt cagcgatcta tttctctttt tc                                 32

<210> SEQ ID NO 24
<211> LENGTH: 25
<212> TYPE: DNA
<213> ORGANISM: Artificial
<220> FEATURE:

```
<223> OTHER INFORMATION: Oligonucleotide as PCR primer designed from the
      upstream region of the alkaline cellulase gene in Bacillus sp.
      KSM-S237 with a insertion of the BamHI restriction site at the
      5'-end

<400> SEQUENCE: 24
cccggatcca acaggcttat attta                                          25

<210> SEQ ID NO 25
<211> LENGTH: 46
<212> TYPE: DNA
<213> ORGANISM: Artificial
<220> FEATURE:
<223> OTHER INFORMATION: Oligonucleotide as PCR primer; 3'-portion from
      the upstream region of the alkaline cellulase gene in Bacillus sp.
      KSM-S237; 5'-portion designed from the alkaline protease gene in
      Bacillus clausii KSM-K16

<400> SEQUENCE: 25
tttccccaac ggtttcttca tattacctcc taaatatttt taaagt                   46

<210> SEQ ID NO 26
<211> LENGTH: 30
<212> TYPE: DNA
<213> ORGANISM: Artificial
<220> FEATURE:
<223> OTHER INFORMATION: Oligonucleotide as PCR primer; 3'-portion from
      nucleotide sequence of the alkaline amylase gene in Bacillus sp.
      KSM-K38; 5'-portion from the alkaline cellulase gene in Bacillus
      sp. KSM-S237

<400> SEQUENCE: 26
gctcttgcag cagatggatt gaacggtacg                                     30

<210> SEQ ID NO 27
<211> LENGTH: 30
<212> TYPE: DNA
<213> ORGANISM: Artificial
<220> FEATURE:
<223> OTHER INFORMATION: Oligonucleotide as PCR primer designed from the
      downstream region of the alkaline amylase gene in Bacillus sp.
      KSM-K38 with a insertion of the XbaI restriction site at the
      5'-end

<400> SEQUENCE: 27
ttggtctaga ccccaagctt caaagtcgta                                     30

<210> SEQ ID NO 28
<211> LENGTH: 29
<212> TYPE: DNA
<213> ORGANISM: Artificial
<220> FEATURE:
<223> OTHER INFORMATION: Oligonucleotide as PCR primer; its 3'-portion
      designed from the alkaline cellulase gene in Bacillus sp. KSM-S237
      and its 5'-portion designed from the alkaline amylase gene in
      Bacillus sp. KSM-K38

<400> SEQUENCE: 28
ttcaatccat ctgctgcaag agctgccgg                                      29
```

MUTANT BACTERIUM BELONGING TO THE GENUS *BACILLUS*

TECHNICAL FIELD

The present invention relates to a host microorganism and a recombinant microorganism, which can be employed to produce useful proteins and polypeptides, and to a method for producing such proteins and polypeptides.

BACKGROUND ART

Microorganisms are widely used for industrially producing a broad range of useful substances, including alcoholic beverages, certain types of foods such as miso (i.e., fermented soybean paste) and shoyu (i.e., soy sauce), amino acids, organic acids, nucleic-acid-related substances, antibiotics, sugars, lipids, and proteins. These substances also find diversified uses, including foods, pharmaceuticals, detergents, products for daily use such as cosmetics, and a variety of chemical raw materials.

In industrial production of useful substances by use of microorganisms, improvement of productivity is one major topic of interest, and one approach therefor is breeding of microorganisms through mutagenesis or other genetic means. Recently, in particular, with advancement of microbial genetics and biotechnology, more efficient production of useful substances through gene recombination techniques attracts attention. In a known method for breeding productive microorganisms by use of gene recombination techniques, a transcription factor which regulates gene expression, in particular an RNA polymerase sigma factor, is potentiated. For example, in *Pseudomonas fluorescens*, the number of copies of a rpoD gene encoding a primary sigma factor (housekeeping sigma factor), which participates in transcription of genes essential to the growth during the vegetative stage, is increased, to thereby increase the production amount of an antibiotic, such as pyoluteorin or 2,4-diacetylphloroglucinol (see, for example, Non-Patent Document 1), and in *Corynebacterium glutamicus*, housekeeping sigA gene is overexpressed, to thereby increase the amount of fermentive production of L-lysine (see, for example, Patent Document 1).

In the above approaches, however, an increased expression of a housekeeping sigma factor is attained during the vegetative stage. Moreover, regarding microorganisms belonging to the genus *Bacillus*, such as *Bacillus subtilis*, no report has so far been published that states augmentation of a sigma factor leads to an increased production of useful substances.
Patent Document 1: WO 2003/054179
Non-Patent document 1: J. Bacteriol., 177, 5387, (1995)

DISCLOSURE OF THE INVENTION

The present invention provides a mutant bacterium produced from a bacterium belonging to the genus *Bacillus* (hereinafter referred to as "a mutant *Bacillus* bacterium"), the mutant *Bacillus* bacterium having, on the genome or a plasmid thereof, a DNA molecule which includes a sigA gene or a gene functionally equivalent thereto and a promoter sequence ligated to the upstream end of the gene, wherein the promoter sequence is recognized and transcribed specifically during the sporulation stage.

The present invention also provides a recombinant microorganism created by transferring, to a mutant *Bacillus* bacterium, a gene encoding a heterologous protein or polypeptide, and a method for producing a protein or polypeptide through use of the recombinant microorganism.

The present invention further provides a method of constructing a mutant *Bacillus* bacterium, characterized in that a microorganism belonging to the genus *Bacillus* is modified so as to have, as a genomic DNA or plasmid DNA, a DNA molecule which includes a sigA gene or a gene functionally equivalent thereto and a promoter sequence ligated to the upstream end of the gene, wherein the promoter sequence is recognized and transcribed specifically during the sporulation stage of the microorganism.

BEST MODE FOR CARRYING OUT THE INVENTION

The present invention is directed to a mutant bacterium which provides enhanced production of a protein or polypeptide; a recombinant microorganism created by transferring, to the mutant *Bacillus* bacterium, a gene encoding a heterologous protein or polypeptide; and a method for producing a protein or polypeptide through use of the recombinant microorganism.

Microorganisms belonging to the genus *Bacillus* have a plurality of sigma factors, each being a subunit of RNA polymerase and participating in the recognition of a promoter sequence. It has been postulated that, when each of different sigma factors which recognize different promoters is bound to an RNA polymerase core complex composed of a plurality of subunits which are not sigma factors, a different gene is transcribed, whereby for each of the thousands of genomic genes, expression is controlled as stipulated by specific conditions. For example, regarding *Bacillus subtilis* belonging to the genus *Bacillus*, 17 sigma factors have been identified. They include SigA (also called a housekeeping sigma factor), which is a primary sigma factor that participates in transcription of a gene which is essential for growth during the vegetative growth period; SigH, SigF, SigE, SigG, and SigK, which control sporulation; SigD, which controls flagellum biogenesis and cell wall lysis; SigL, which controls metabolism of certain amino acids or saccharides; SigB, which controls the ability of adjustment to environmental changes; and a sigma factor named ECF sigma (*Bacillus subtilis* and Its Closest Relatives: From Genes to Cells, Edited by A. L. Sonenshein, American Society for Microbiology, pp 289, (2002)).

Figure 1:
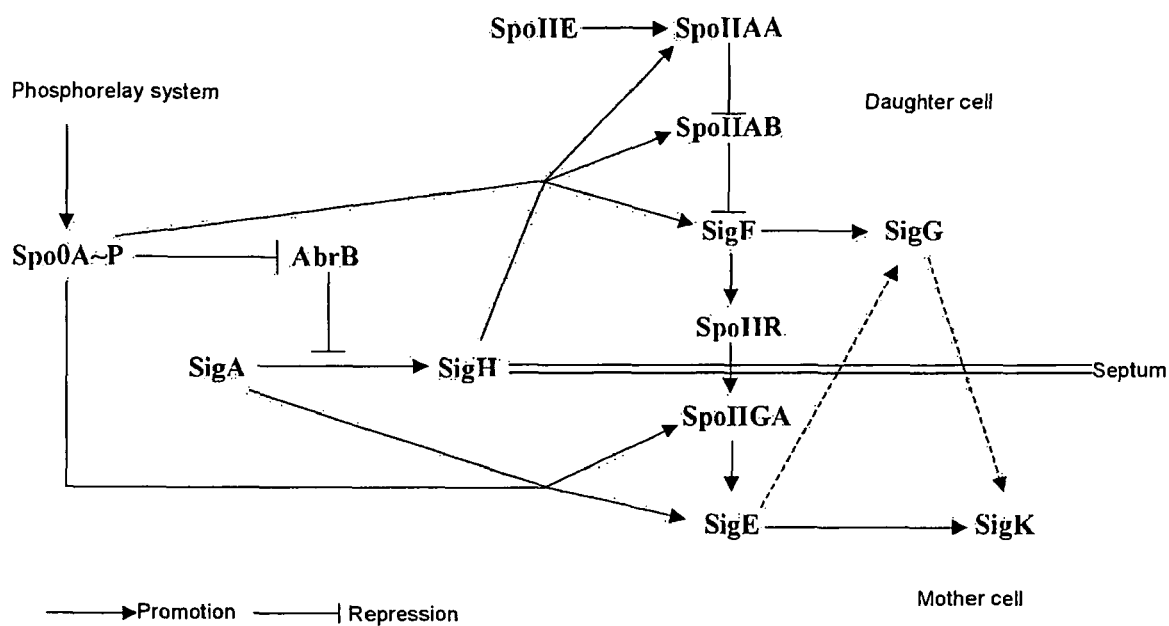
FIG. 1 A chart showing sequential activation of sigma factors during the sporulation stage.

Of the above sigma factors, those that control over the sporulation stage are known to be sequentially expressed and activated as the sporulation process advances as shown in FIG. 1. Specifically, when *Bacillus subtilis* falls into a shortage of nutrients, firstly, phosphorylation of Spo0A, a sporulation initiation control factor, occurs via a multi-step phosphate transport system—also called the phosphate relay system—provided for a plurality of proteins (Cell, 64, 545, (1991)). As the phosphorylated Spo0A (Spo0A-P) level elevates, repressor AbrB, which represses expression of sigH, the structural gene of SigH, is less induced, and as a result, transcription of sigH is induced to become SigA-dependent (J. Bacteriol., 173, 521, (1991)). Once SigH has been activated, through asymmetrical membrane formation, the cytoplasm of *Bacillus subtilis* is divided into compartments of mother cell side and daughter cell side. Subsequently, on the daughter cell side, Spo0A-P and SigH cooperate to induce transcription of an operon (spoIIAA-spoIIAB-sigF) which contains sigF, a structural gene of SigF (Gene, 101, 113, (1991)), and on the mother cell side, Spo0A-P and SigA cooperate to induce transcription of an operon (spoIIGA-sigE) which contains sigE, a structural gene of a SigE precursor (J. Bacteriol., 169, 3329, (1987)). Activation of SigF is controlled by an anti-sigma factor SpoIIAB and an anti-anti-sigma factor SpoIIAA, and also by SpoIIE, which is a dephosphorylase for SpoIIAA (Genes Cells, 1, 881 (1996)). Activated SigF induces transcription of spoIIR, a structural gene of a signal transduction protein SpoIIR. SpoIIR secreted from the daughter cell side activates SpoIIGA, which is a SigE precursor activating protease localized in the asymmetrical membrane on the mother cell side, presumably leading to activation of SigE (Proc. Natl. Acad. Sci. U.S.A., 92, 2012, (1995)).

Moreover, on the daughter cell side, SigF induces transcription of sigG, a structural gene of SigG, while on the mother cell side, SigE induces transcription of sigK, a structural gene of SigK. Activation of SigG on the daughter cell side occurs after the SigE activation has taken place on the mother cell side. Afterwards, activation of SigK on the mother cell side occurs (Mol. Microbiol., 31, 1285, (1999)).

During vegetative growth, through association with an RNA polymerase core complex, SigA is reported to predominantly direct transcription of a gene having a SigA-recognizable promoter, or an operon. During sporulation, when other sigma factors are activated through the above-mentioned mechanism, substitution takes place to replace the sigma factor that is associated with the RNA polymerase core complex, resulting in a relative decrease in the amount of SigA-associated RNA polymerase (J. Bacteriol., 179, 4969 (1999)). Thus, during and after the sporulation stage, the level of transcription from a SigA-recognized promoter is considered to decrease as compared with the level during the vegetative growth stage.

Under such circumstances, the present inventors have found that, through ligating a promoter sequence recognized and expressed specifically during the sporulation stage to a gene encoding SigA which is a main sigma factor relating to transcription of genes essential in growth mainly during the vegetative stage, expression of the gene encoding SigA can be enhanced during the sporulation stage which follows the vegetative stage and level of binding between the sigma factor and an RNA polymerase core complex can be enhanced, to thereby increase productivity of a heterologous protein or polypeptide after the sporulation stage can be enhanced.

When the microorganism of the present invention is employed, the above heterologous protein or polypeptide can be produced efficiently.

In the present invention, homology between amino acid sequences and that between nucleic acid sequences are both determined by use of the Lipman-Pearson method (Science, 227, 1435 (1985)). Specifically, calculation is performed by use of a homology analysis program (Search Homology) developed by genetic information processing software Genetyx-Win, (Software Development Co., Ltd.), with ktup (the unit size to be compared) being set to 2.

The mutant Bacillus bacterium of the present invention is constructed such that DNA having a promoter sequence which is recognized and transcribed specifically during the sporulation stage and which is ligated to an upstream end of a sigA gene or a gene equivalent thereto is present on the genome or a plasmid thereof.

No particular limitation is imposed on the origin of a parent microorganism employed for constructing such a mutant Bacillus bacterium, so long as the parent microorganism is a bacterium belonging to the genus Bacillus exhibiting a unique feature of sporulation, and a wild type microorganism or a mutant microorganism may be employed. Preferred examples of bacteria belonging to the genus Bacillus employed in the present invention include Bacillus subtilis, Bacillus cereus, and Bacillus halodulans, whose complete genomic information has already been obtained. In particular, Bacillus subtilis is preferred from the viewpoint that genetic engineering techniques and genomic engineering techniques for this microorganism have been established, and that the microorganism has ability to secrete the produced protein extracellularly.

As used herein, a sigA gene of Bacillus subtilis refers to a gene encoding an amino acid sequence represented by SEQ ID NO: 1. A gene equivalent to the sigA gene refers to a gene encoding an amino acid sequence having a homology of 70% or more to the amino acid sequence represented by SEQ ID NO: 1, preferably 80% or more, more preferably 90% or more, still more preferably 95% or more, yet still more preferably 98% or more.

In the present invention, a promoter sequence recognized and transcribed specifically during the sporulation stage is ligated to an upstream end of such a sigA gene or a gene equivalent thereto. The promoter sequence, which is recognized and transcribed specifically during the sporulation stage, may be any of a naturally derived sequence, a modified naturally derived sequence, and a chemically synthesized sequence.

Examples of the promoter sequences employed for creating a mutant Bacillus subtilis include a promoter sequence having a characteristic feature described in any one of (1) to (6).

(1) a promoter sequence whose transcription repression by AbrB is canceled as Spo0A-P level increases and which is recognized and transcribed by SigA (2) a promoter sequence which is recognized and transcribed by SigH (3) a promoter sequence which is recognized and transcribed by SigF (4) a promoter sequence which is recognized and transcribed by SigE (5) a promoter sequence which is recognized and transcribed by SigG (6) a promoter sequence which is recognized and transcribed by SigK It is generally accepted that a sigma factor is bound to a sequence of several bases that is present in the vicinity of a 10-base upstream site or 35-base upstream site from the transcription start point. The sequences corresponding to these sites are called the −10 region and the −35 region, respectively. Moreover, it has been known that, for each sigma factor, common characteristics are shared by the base sequence and the distance between the two regions. Thus, such a sequence is called a consensus sequence. Therefore, examples of the promoter sequences (1) to (6) include (1') a sequence whose transcription repression by AbrB is canceled as Spo0A-P level increases and having a consensus sequence which is recognized by SigA, (2') a sequence having a consensus sequence which is recognized by SigH, (3') a sequence having a consensus sequence which is recognized by SigF, (4') a sequence having a consensus sequence which is recognized by SigE, (5') a sequence having a consensus sequence which is recognized by SigG, (6') a sequence having a consensus sequence which is recognized by SigK.

The consensus sequences which have heretofore been reported for the sigma factors of Bacillus subtilis are shown in Table 1.

TABLE 1

| Sigma factor | Consensus sequence | | |
|---|---|---|---|
| | −35 region | Distance between two regions | −10 region |
| SigA | TTGaca | 14 | tgnTAtaat |
| SigH | RnAGGwWW | 11-12 | RnnGAAT |
| SigF | GywTA | 15 | GgnrAnAnTw |
| SigE | Ata | 16-18 | cATAcanT |
| SigG | gnATr | 15 | cAtnnTA |
| SigK | AC | 16-18 | CATAnnnT |

(*Bacillus subtilis* and Its Closest Relatives: From Genes to Cells, Edited by A. L. Sonenshein, American Society for Microbiology, pp 289, (2002))

In the above listed sequences, R denotes A or G, W denotes A or T, and N denotes any nucleotides, and when nucleotides are shown with upper case letters, the nucleotides are highly conserved, whereas when nucleotides are shown with lower case letters, the nucleotides are not well conserved.

A sequence which is recognized and bound by AbrB, which have been reported, is represented by a nucleotide sequence of WaWWtttWCAAaaaaW (W denotes A or T, and when nucleotides are shown with upper case letters, the nucleotides are highly conserved, whereas when nucleotides are shown with lower case letters, the nucleotides are not well conserved (J. Bacteriol., 177, 6999, (1995)).

As described above, a promoter sequence recognized and transcribed specifically during the sporulation stage in the present invention has a sequence of any one of the above (1) to (6) and (1') to (6').

Examples of the promoter having a trait of (1) or (1') and originating from nature include promoters for a gene or an operon of *Bacillus subtilis* listed in Table 2; examples of the promoter having a trait of (2) or (2') and originating from nature include promoters for a gene or an operon of *Bacillus subtilis* listed in Table 3; examples of the promoter having a trait of (3) or (3') and originating from nature include promoters for a gene or an operon of *Bacillus subtilis* listed in Table 4; examples of the promoter having a trait of (4) or (4') and originating from nature include promoters for a gene or an operon of *Bacillus subtilis* listed in Table 5; examples of the promoter having a trait of (5) or (5') and originating from nature include promoters for a gene or an operon of *Bacillus subtilis* listed in Table 6; and examples of the promoter having a trait of (6) or (6') and originating from nature include promoters for a gene or an operon of *Bacillus subtilis* listed in Table 7.

The names, numbers, and functions of respective genes in the Tables contained herein conform with the *Bacillus subtilis* genome data reported in Nature, 390, 249 to 256 (1997) and made public by JAFAN (Japan Functional Analysis Network for *Bacillus subtilis*; BSORF DB) on the Internet by inserting bacillus.genome.ad.jp/ renewed Jun. 17, 2003 after the hypertext transfer protocol http://.

TABLE 2

| Gene name | Gene No. |
|---|---|
| sigH | BG10159 |
| spo0E | BG10769 |
| aprE | BG10190 |
| sinI | BG10753 |
| dppA | BG10842 |
| abrB | BG10100 |

TABLE 2-continued

| Gene name | Gene No. |
|---|---|
| ftsA | BG10231 |
| pbpE | BG10390 |
| kinB | BG10745 |

(*Bacillus subtilis* and other gram-positive bacteria: biochemistry, physiology, and molecular genetics, Edited by A. L. Sonenshein, American Society for Microbiology, pp 757, (1993), J. Bacteriol., 177, 6999, (1995))

In the above Table, when an operon is referred to, the name of the first gene of the transcription unit is given.

TABLE 3

| Gene name | Gene No. |
|---|---|
| sigA | BG10314 |
| spo0M | BG12229 |
| spoVG | BG10112 |
| citG | BG10384 |
| spo0F | BG10411 |
| spoVS | BG11245 |
| ureA | BG11981 |
| yvyD | BG10740 |
| spo0A | BG10765 |
| ftsA | BG10231 |
| kinA | BG10204 |
| spoIIAA | BG10296 |
| minC | BG10329 |
| phrC | BG11959 |
| ytxG | BG10974 |

(*Bacillus subtilis* and Its Closest Relatives: From Genes to Cells, Edited by A. L. Sonenshein, American Society for Microbiology, pp 289, (2002))

In the above Table, when an operon is referred to, the name of the first gene of the transcription unit is given.

TABLE 4

| Gene name | Gene No. |
|---|---|
| dacF | BG10295 |
| bofC | BG11917 |
| gerAA | BG10385 |
| gpr | BG10438 |
| katX | BG11945 |
| sspN | BG14179 |
| spoIIQ | BG11978 |
| spoIIR | BG10937 |
| spoIIIG | BG10236 |
| spoIVB | BG10311 |
| ywhE | BG12459 |
| yhcN | BG11592 |
| lonB | BG11077 |

(*Bacillus subtilis* and Its Closest Relatives: From Genes to Cells, Edited by A. L. Sonenshein, American Society for Microbiology, pp 289, (2002))

In the above Table, when an operon is referred to, the name of the first gene of the transcription unit is given.

TABLE 5

| Gene name | Gene No. |
|---|---|
| spoIIP | BG10439 |
| spoIID | BG10766 |
| spoIIM | BG10768 |

TABLE 5-continued

| Gene name | Gene No. |
| --- | --- |
| bofA | BG10087 |
| spoIIIAA | BG10540 |
| spoIIID | BG10408 |
| spoIVFA | BG10331 |
| cotE | BG10494 |
| cotJA | BG11799 |
| dacB | BG10527 |
| spoIVA | BG10275 |
| spoIVCB | BG10459 |
| spoVB | BG10778 |
| spoVD | BG10222 |
| spoVE | BG10226 |
| spoVK | BG11039 |
| spoVM | BG10776 |
| spoVR | BG10182 |
| spoVID | BG10346 |
| glgB | BG10907 |
| mmgA | BG11319 |
| phoB | BG10697 |
| yknT | BG12251 |
| yteV | BG12339 |
| safA | BG13781 |
| yaaH | BG10080 |
| cwlD | BG11514 |
| cwlJ | BG11172 |
| yjmC | BG13206 |
| yfhS | BG12892 |
| yoaW | BG13493 |

(*Bacillus subtilis* and Its Closest Relatives: From Genes to Cells, Edited by A. L. Sonenshein, American Society for Microbiology, pp 289, (2002))

In the above Table, when an operon is referred to, the name of the first gene of the transcription unit is given.

TABLE 6

| Gene name | Gene No. |
| --- | --- |
| gerAA | BG10385 |
| gerBA | BG10640 |
| gerD | BG10644 |
| csgA | BG11504 |
| bofC | BG11917 |
| dacF | BG10295 |
| gpr | BG10438 |
| spoVAA | BG10892 |
| spoIIIG | BG10236 |
| spoVT | BG10119 |
| sspA | BG10786 |
| sspB | BG10787 |
| sspC | BG10882 |
| sspD | BG10788 |
| sspE | BG10789 |
| sspF | BG10108 |
| sspJ | BG14174 |
| sleB | BG11439 |
| splA | BG10202 |
| sspN | BG14179 |
| spoIVB | BG10311 |
| sspH | BG12917 |
| sspL | BG14176 |
| ybaK | BG11503 |
| yhcN | BG11592 |
| ywhE | BG12459 |
| ycxE | BG11066 |
| sspI | BG12318 |
| sspK | BG14175 |
| sspM | BG14177 |
| sspO | BG11920 |
| cwlD | BG11514 |

(*Bacillus subtilis* and Its Closest Relatives: From Genes to Cells, Edited by A. L. Sonenshein, American Society for Microbiology, pp 289, (2002))

In the above Table, when an operon is referred to, the name of the first gene of the transcription unit is given.

TABLE 7

| Gene name | Gene No. |
| --- | --- |
| cgeA | BG11193 |
| cgeC | BG11195 |
| cwlC | BG10825 |
| cotA | BG10490 |
| cotB | BG10491 |
| cotC | BG10492 |
| cotD | BG10493 |
| cotE | BG10494 |
| cotF | BG10012 |
| cotH | BG11791 |
| cotM | BG11822 |
| cotT | BG10495 |
| cotG | BG11017 |
| cotSA | BG11381 |
| cotV | BG10496 |
| cotX | BG10500 |
| cotY | BG10498 |
| yobW | BG12269 |
| yqeE | BG11633 |
| spoIVCB | BG10459 |
| spoVK | BG11039 |
| spoVFA | BG10781 |
| gerE | BG10355 |
| sspG | BG14173 |
| yfhP | BG12890 |
| yabG | BG10106 |

(*Bacillus subtilis* and Its Closest Relatives: From Genes to Cells, Edited by A. L. Sonenshein, American Society for Microbiology, pp 289, (2002))

In the above Table, when an operon is referred to, the name of the first gene of the transcription unit is given.

As described above, preferred examples of the promoter sequence recognized and transcribed during the sporulation stage employed in the present invention include promoters having a sequence of any one of (1) to (6) and (1') to (6'). In *Bacillus subtilis*, it is reported that SigE exhibits higher affinity with RNA polymerase as compared with SigA (J. Bacteriol., 179, 4969, (1999)). Therefore, more preferably, a promoter whose transcription is activated prior to activation of SigE is employed. Examples of more preferred promoter sequences include a promoter sequence whose transcription repression by AbrB is canceled as Spo0A-P level increases and which is recognized and transcribed by SigA (namely, (1) or (1')) and a promoter sequence which is recognized and transcribed by SigH (namely, (2) or (2')).

Examples of the promoter having a sequence of (1) or (1') and originating from nature include promoter sequences for expressing a gene or an operon of *Bacillus subtilis* listed in Table 1. Of these, preferred promoters include a promoter sequence for a sigH of *Bacillus subtilis*. The promoter sequence for the sigH of *Bacillus subtilis* contains, in the nucleotide sequence represented by SEQ ID NO: 2, a nucleotide sequence ranging from base Nos. 987 to 1,027, preferably a nucleotide sequence ranging from base Nos. 987 to 1047, more preferably a nucleotide sequence ranging from base Nos. 1 to 1,047; has a base length of 5,000 bp or less, preferably 2,000 bp or less, more preferably 1,047 bp or less; and has promoter functions equivalent to those of a promoter for expressing the sigH of *Bacillus subtilis*.

Examples of the promoter having a sequence of (2) or (2') and originating from nature include promoter sequences for expressing a gene or an operon of *Bacillus subtilis* listed in Table 2. Of these, preferred promoters include a promoter sequence for expressing a spoIIAA-spoIIAB-sigF operon (spoIIA operon) of *Bacillus subtilis*. The promoter sequence for expressing the spoIIA operon of *Bacillus subtilis* contains, in the nucleotide sequence represented by SEQ ID NO: 3, a nucleotide sequence ranging from base Nos. 1,081 to 1,110, preferably a nucleotide sequence ranging from base Nos. 1,081 to 1,118, more preferably a nucleotide sequence ranging from base Nos. 1 to 1,143; has a base length of 5,000 bp or less, preferably 2,000 bp or less, more preferably 1,143 bp or less; and has promoter functions equivalent to those of a promoter for expressing the sigH of *Bacillus subtilis*.

The promoter sequence recognized and expressed specifically during the sporulation stage employed in the present invention includes a sequence virtually equivalent to the promoter sequence for expressing a gene or an operon of *Bacillus subtilis* listed in Tables 1 to 6. For example, a sequence corresponding to the promoter sequence for expressing the sigH of *Bacillus subtilis* includes a DNA fragment containing, in the nucleotide sequence represented by SEQ ID NO: 2, a nucleotide sequence ranging from base Nos. 987 to 1,027, preferably a nucleotide sequence ranging from base Nos. 1,081 to 1,118, more preferably a nucleotide sequence ranging from base Nos. 1 to 1,143, these sequences having one or more substituted, deleted, or inserted nucleotides; having a base length of 5,000 bp or less, preferably 2,000 bp or less, more preferably 1,047 bp or less; and having promoter functions equivalent to those of a promoter for expressing the sigH of *Bacillus subtilis*.

Also, a sequence corresponding to the promoter sequence for expressing the spoIIA operon includes a DNA fragment containing, in the nucleotide sequence represented by SEQ ID NO: 3, a nucleotide sequence ranging from base Nos. 1,081 to 1,110, preferably a nucleotide sequence ranging from base Nos. 1,081 to 1,118, more preferably a nucleotide sequence ranging from base Nos. 1 to 1,143, these sequences having one or more substituted, deleted, or inserted nucleotides; having a base length of 5,000 bp or less, preferably 2,000 bp or less, more preferably 1,118 bp or less; and having promoter functions equivalent to those of a promoter for expressing the above-mentioned operon.

The promoter sequence employed in the present invention which is recognized by a sigma factor relating specifically to transcription during the sporulation stage includes promoter sequences for expressing ortholog genes of a gene of *Bacillus subtilis* or each of some genes constituting an operon of *Bacillus subtilis*, listed in Tables 2 and 3. The ortholog genes are preferably derived from bacteria belonging to the genus *Bacillus*. The ortholog genes can be located by use of a Create/view Orthologous gene table program of Microbial Genome Database (MBGD, available by inserting mbgd-.genome.ad.jp/ after the hypertext transfer protocol http://) published on the interne. Examples of the ortholog genes of the sigH gene of *Bacillus subtilis* include a sigH (BH0115) gene of *Bacillus halodulans* and a BC0114 gene of *Bacillus cereus*. Examples of the ortholog genes of each of some genes constituting the spoIIA operon of *Bacillus subtilis* include a sigF (BH1538) gene, a spoIIAB (BH1537) gene, and a spoI-IAA (BH1536) gene, these three genes being of *Bacillus halodulans*; and a BC4072 gene, a BC4073 gene, and a BC4074 gene, these three genes being of *Bacillus cereus*.

As a promoter sequence which is recognized by a sigma factor participating specifically in transcription at the sporulation stage, the above promoter sequences may be employed singly or in combination of two or more species.

DNA having a promoter sequence which is recognized and transcribed specifically during the sporulation stage and which is ligated to an upstream end of the sigA gene of *Bacillus subtilis* or a gene equivalent thereto can be constructed on the genome thereof through inserting a DNA fragment containing the promoter sequence recognized and transcribed specifically during the sporulation stage to an upstream site or downstream site of a SigA-recognized promoter sequence which is present at an upstream end of the sigA gene originally present on the genome of *Bacillus subtilis*. The DNA fragment containing the promoter sequence recognized and transcribed specifically during the sporulation stage may be inserted into any site which is located upstream of the sigA gene or a gene equivalent thereto. Preferably, the site is located in a region of 2,000 bp or less flanking an upstream side of a sigA structural gene, more preferably a region of 1,000 bp or less, still preferably a region of 500 bp or less, yet preferably a region of 1 to 198 bp. When the DNA fragment, which contains the promoter sequence recognized and transcribed specifically during the sporulation stage, has no proper sequence to be bound by ribosomes, the DNA fragment is preferably inserted into a region of 15 bp or more upstream of the sigA structural gene.

Alternatively, the aforementioned DNA, which has a promoter sequence recognized and transcribed specifically during the sporulation stage and which is ligated to an upstream end of the sigA gene or a gene equivalent thereto, can be constructed through PCR or other methods. Preferably, a sequence between a site ligated by the DNA fragment and the sigA structural gene; i.e., a sequence located upstream of the sigA gene which is originally present in the genome of *Bacillus subtilis*, has 0 to 2000 base pairs, more preferably 0 to 1000 base pairs, still preferably 0 to 500 base pairs, yet preferably 0 to 198 base pairs. When the DNA fragment, which has the promoter sequence recognized and transcribed specifically during the sporulation stage, contains no proper sequence to be bound by ribosomes, the above sequence between a site ligated by the DNA fragment and the sigA structural gene; i.e., a sequence located upstream of the sigA gene which is originally present in the genome of *Bacillus subtilis*, has preferably 15 base pairs or more. In order to construct the mutant *Bacillus* bacterium of the present invention, DNA which is constructed through the above method may be introduced into a parent bacterium belonging to the genus *Bacillus*.

For example, a DNA fragment having a promoter sequence recognized and transcribed specifically during the sporulation stage may be ligated to a DNA fragment having a sigA gene and other genes through PCR; the thus-produced DNA fragment may be introduced into a plasmid vector capable of replicating in a parent bacterium belonging to the genus *Bacillus* through cloning; and the plasmid vector may be introduced into the parent bacterium belonging to the genus *Bacillus*. When *Bacillus subtilis* is employed as the parent bacterium belonging to the genus *Bacillus* employed for constructing the mutant *Bacillus* bacterium of the present invention, a variety of plasmid vectors, which had been reported, capable of replicating in a *Bacillus subtilis* cell may be employed. Examples of the plasmid vectors include pUB110 (Plasmid, 15, 93, (1986)), pC194 (J. Bacteriol., 150, 815, (1982)), and pTX14-3 (Plasmid, 30, 119, (1993)).

Alternatively, homologous recombination or similar techniques may be used to introduce, to the genome, a DNA fragment produced by ligating a DNA fragment containing a promoter sequence specifically recognized and transcribed during the sporulation stage to an upstream site of a DNA fragment containing, for example, a sigA gene. Several methods have already been reported for introducing a DNA fragment into the genome through homologous recombination (for example, Mol. Gen. Genet., 223, 268 (1990)). The mutant *Bacillus* bacterium may be produced through these methods.

Next will be described in more detail a method for ligating a DNA fragment containing a promoter sequence recognized and transcribed during the sporulation stage to a DNA fragment containing a sigA gene through the SOE (splicing by overlap extension)-PCR method (Gene, 77, 51, 1989), to thereby prepare a DNA fragment; and introducing the thus-prepared DNA fragment on the genome through homologous recombination. However, in the present invention, the method for introducing the DNA fragment is not limited only to the below-described method.

Figure 2:
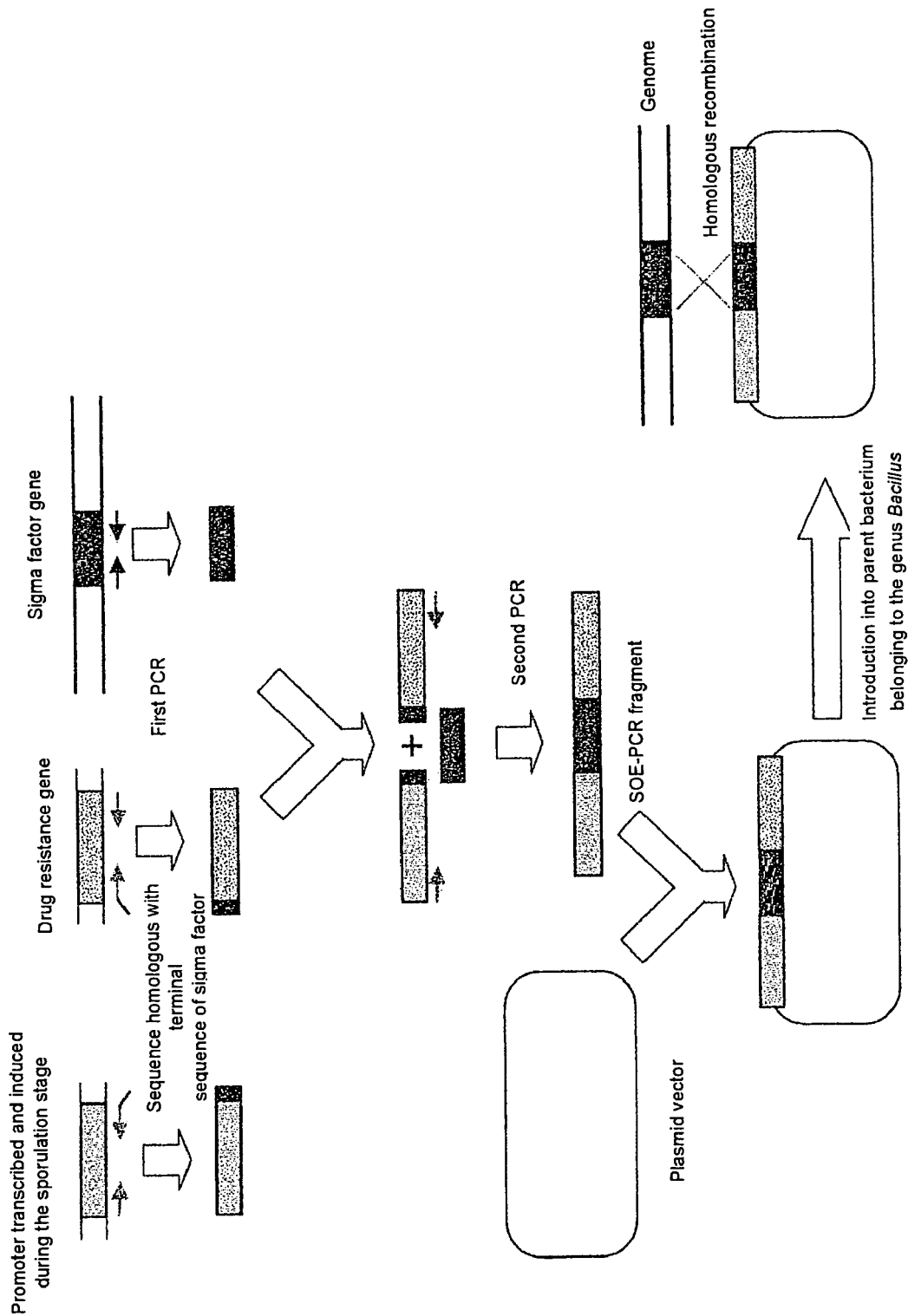
FIG. 2 A conceptual diagram showing an exemplary process for constructing the sigA gene of the present invention.

In the present invention, in the first PCR, the following three fragments are prepared: a DNA fragment containing a promoter sequence recognized and transcribed specifically during the sporulation stage, a structural gene fragment of a housekeeping sigma factor, and a drug resistant marker gene. The primers to be used in this step may, for example, be those specifically designed so that an upstream 10 to 30 base pair sequence of the structural gene fragment of a housekeeping sigma factor is added to the downstream end of the DNA fragment containing the promoter sequence, and a downstream 10 to 30 base pair sequence of the structural gene fragment of the housekeeping sigma factor is added to the upstream end of the drug resistance marker gene (FIG. 2).

Next, using three PCR fragments prepared in the first PCR as templates, the second PCR is performed by use of an upstream primer of the fragment containing the promoter sequence and a downstream primer of the drug resistance marker gene fragment. As a result, one end of sigA gene fragment anneals with the downstream end of the fragment containing the promoter sequence through the overlapping sequences, and the other end of sigA gene fragment anneals with the upstream end of the drug resistance marker gene fragment through the overlapping sequences. Through PCR amplification, there can be obtained a DNA fragment in which the promoter sequence, which is recognized by a sigma factor relating specifically to transcription during the sporulation stage, is ligated to an upstream end of the sigA gene and the drug resistance marker gene is ligated downstream thereto (FIG. 2).

When a sigH gene of *Bacillus subtilis* or a promoter for expressing the spoIIA operon is employed as a promoter recognized and transcribed specifically during the sporulation stage and when a chloramphenicol-resistant gene is employed as a drug resistance marker gene, a target DNA fragment can be obtained through SOE-PCR under typical conditions described in literature (see, for example, PCR Protocols. Current Methods and Applications, Edited by B. A. White, Humana Press, pp. 251 (1993), Gene, 77, 61, 1989), by use of a primer set such as that shown in Table 8 and a conventional enzyme kit for PCR (e.g., Pyrobest DNA Polymerase (Takara Shuzo)).

The thus-obtained DNA fragment may be introduced into the genome of, for example, *Bacillus subtilis* as follows. The DNA fragment is introduced into a plasmid vector incapable of replicating in a *Bacillus subtilis* cell (e.g.; pMW219 (NIPPON GENE)) through cloning; the plasmid vector is introduced into cells through the competent method or any suitable method, to thereby cause homologous recombination between a gene region encoding a housekeeping sigma factor on the plasmid and a sigA gene region on the genome; and, by use of a drug resistance marker as an indicator, there can be selected cells having on the genome the DNA fragment containing a sigA gene ligated to a promoter recognized and transcribed specifically during the sporulation stage and a plasmid vector (FIG. 2). Specifically, when a DNA fragment which had been prepared by use of a primer set shown in Table 3 is introduced into pMW219 through cloning, and the thus-obtained plasmid is introduced into a *Bacillus subtilis* cell, colonies grown in an agar medium supplemented with chloramphenicol are separated; and through PCR employing genomic DNA as a template or any suitable method, introduction, onto the genome, of the DNA fragment having the sigA gene ligated to a promoter region of the sigH gene or the spoIIA operon can be confirmed In the above procedure, *Bacillus subtilis* is employed as a parent bacterium belonging to the genus *Bacillus*. However, alternatively the mutant *Bacillus* bacterium of the present invention may be obtained in a similar manner from other bacteria belonging to the genus *Bacillus*.

Using a mutant *Bacillus* bacterium produced in the aforementioned manner, expression of SigA which transcribes genes encoding heterologous proteins or polypeptides, and a variety of genes relating to production of proteins can be enhanced, leading to improvement in production of the heterologous proteins or polypeptides.

Specifically, genes encoding target proteins or polypeptides are ligated downstream of a promoter recognized by SigA, and the product is introduced into the mutant *Bacillus* bacterium of the present invention, whereby the target proteins or polypeptides is produced not only during the vegetative stage but also during the sporulation stage, resulting in enhanced production of the target proteins or polypeptides, as compared with a parent bacterium belonging to the genus *Bacillus*.

No particular limitation is imposed on the gene encoding the target protein or polypeptide. Examples of the protein and polypeptide include physiologically-active peptides and enzymes for industrial purposes such as detergents, foods, fibers, feeds, chemicals, medicine, and diagnostic agents. Industrial enzymes may be functionally grouped into oxidoreductases, transferases, hydrolases, lyases, isomerases, and ligases/synthetases. Preferably, hydrolases such as cellulase, α-amylase, and protease may be used. Specific examples include cellulase belonging to family 5 in the classification of enzymes which hydrolyze polysaccharides (Biochem. J., 280, 309, (1991)); in particular, cellulase derived from a microorganism, more particularly cellulase derived from the genus *Bacillus*. Examples include alkaline cellulase having an amino acid sequence represented by SEQ ID NO: 4 which is derived from *Bacillus* sp. KSM-S237 (FERM BP-7875), alkaline cellulase having an amino acid sequence represented by SEQ ID NO: 6 which is derived from *Bacillus* sp. KSM-64 (FERM BP-2886), and cellulase which has another amino acid sequence having a homology of 70% to said amino acid sequence, preferably 80% or more, more preferably 90% or more, further preferably 95% or more, or still further preferably 98% or more.

Specific examples of α-amylase include α-amylase derived from a microorganism, preferably liquefied amylase derived from the genus *Bacillus*. Examples include alkaline amylase having an amino acid sequence represented by SEQ ID NO: 19 which is derived from *Bacillus* sp. KSM-K38 (FERM BP-6946), and amylase which has another amino-acid sequence having a homology of 70% or more to said amino-acid sequence, preferably 80% or more, more preferably 90% or more, further preferably 95% or more, or even more preferably 98% or more. The homology of the amino-acid sequence is calculated by the Lipman-Pearson method (Science, 227, 1435 (1985)). Specific examples of protease include serine protease and metalloprotease which are derived from microorganisms, particularly those belonging to the genus *Bacillus*. Examples include alkaline protease having an amino acid sequence represented by SEQ ID NO: 21 which is derived from *Bacillus clausii* KSM-K16 (FERM BP-3376), and protease which has another amino-acid sequence having a homology of 70% or more to said aminoacid sequence, preferably 80% or more, more preferably 90% or more, further preferably 95% or more, or even more preferably 98% or more.

As described above, the promoter sequence recognized by a housekeeping sigma factor (e.g., SigA of *Bacillus subtilis*) must be ligated to an upstream end of the gene of the target protein or polypeptide. In addition, preferably, regulatory regions related to translation or secretion; i.e., a site bound by ribosomes, a translation initiation region including the initiation codon, and a secretion signal peptide region, are properly ligated to the gene of the target protein or polypeptide. In one preferred example, a transcription initiation regulatory region containing a promoter transcribed by a housekeeping sigma factor, a translation initiation region, and a secretion signal peptide region of a cellulase gene derived from a microorganism belonging to the genus *Bacillus* disclosed in, for example, JP-A-2000-210081 or JP-A-1992-190793; i.e., a cellulase gene derived from KSM-S237 (FERM BP-7875) or KSM-64 (FERM BP-2886), are properly ligated to a structural gene of the target protein or polypeptide. More specifically, preferred DNA fragments to be ligated include a nucleotide sequence ranging from base Nos. 1 to 659 in SEQ ID NO: 5; a nucleotide sequence ranging from base Nos. 1 to 696 of a cellulase gene represented by SEQ ID NO: 7; a DNA fragment having a nucleotide sequence having a homology of 70% or more to any one of said nucleotide sequences, preferably 80% or more, more preferably 90% or more, further preferably 95% or more, even more preferably 98% or more; or a DNA fragment having a nucleotide sequence lacking a portion of any one of said nucleotide sequences. Preferably, one of these DNA fragments is properly ligated to a structural gene of the target protein or polypeptide.

Productivity of the target protein or polypeptide can be enhanced by transferring a recombinant plasmid having a DNA fragment including a gene encoding the target protein or polypeptide ligated to a proper plasmid vector into the mutant *Bacillus* bacterium of the present invention through a conventional transformation technique. Alternatively, the DNA fragment is ligated to a proper region which is homologous with the genome of the mutant *Bacillus* bacterium of the present invention, to thereby a DNA fragment. The DNA fragment is inserted directly into the genome of the mutant *Bacillus* bacterium of the present invention, whereby productivity of the target protein or polypeptide may be enhanced.

The target protein or polypeptide obtained by use of the mutant *Bacillus* bacterium of the present invention as a host cell may be produced in such a manner that corresponding cells are inoculated onto a culture medium containing assimilable carbon sources and nitrogen sources, and other essential components; the cells are cultured through a conventional microorganism culturing method; and subsequently, protein or polypeptide is collected and purified.

In the aforementioned manner, a bacterium belonging to the genus *Bacillus*, which exhibits enhanced efficiency in transcription of the sigA gene during the sporulation stage, can be constructed. When the mutant *Bacillus* bacterium is employed as a host cell for production through a recombinant technique, useful proteins and polypeptides may be produced efficiently.

Next, a method for constructing the mutant bacterium belonging to genus *Bacillus* of the present invention and a method for producing cellulase by use of the same mutant bacterium as a host cell will be described in detail by way of Examples.

EXAMPLES

Example 1

Construction of Plasmid Employed in Introducing into the Genome of *Bacillus subtilis*, a sigA Gene Containing Promoter Transcribed Specifically During the Sporulation Stage Construction of a plasmid was performed. The plasmid was employed in introducing a DNA fragment having a promoter for expressing a sigH gene or a promoter for expressing a spoIIA operon ligated to an upstream end of a sigA structural gene into the genome of *Bacillus subtilis* through single crossing over homologous recombination in accordance with the procedure as shown in FIG. 2. Specifically, a genome DNA sample, serving as a template, extracted from *Bacillus subtilis* 168 and a primer set of sigAf and sigAr shown in Table 8 were employed, to thereby prepare a 1.2 kb fragment (A) having a sigA gene through PCR. In the same manner above, a primer set of sigHUf and sigHUr-sigA shown in Table 8 was employed, to thereby prepare a 1.0 kb fragment (B) containing a sigH gene promoter flanking the upstream side of the sigH gene on the genome. In the same manner above, a primer set of sigFUf and sigFUr-sigA shown in Table 8 was employed, to thereby prepare a 1.1 kb fragment (C) containing a spoIIA operon promoter flanking the upstream region of the spoIIA operon on the genome and controlling transcription of a sigF gene. A plasmid pC194 (J. Bacteriol. 150 (2), 815 (1982)) serving as a template and a primer set of CmFW and Cmr-sigA shown in Table 8 were used to prepare a 0.9 kb fragment (D) containing a chloramphenicol-resistant gene. Subsequently, SOE-PCR was performed by use of a primer set of sigHUf and CmFW shown in Table 8, and the thus-prepared three fragments (A), (B), and (D) in combination as templates, to thereby produce a 3.1 kb DNA fragment (E) in which the three fragments (B), (A), and (D) were ligated in this sequence; i.e., the promoter for expressing the sigH gene was ligated to an upstream end of the sigA structural gene, and the chloramphenicol-resistant gene was ligated, in a reverse direction, downstream of the sigA structural gene. In the same manner, SOE-PCR was performed by use of a primer set of sigFUf and CmFW shown in Table 8, and by use of the three fragments (A), (C), and (D) in combination as templates, to thereby prepare a 3.2 kb DNA fragment (F) in which the three fragments (C), (A), and (D) were ligated in this sequence; i.e., the spoIIA operon promoter was ligated to an upstream end of the sigA structural gene, and the chloramphenicol-resistant gene was ligated, in a reverse direction, downstream of the sigA structural gene. The thus-prepared 3.1 kb DNA fragment (E) and 3.2 kb DNA fragment (F) were individually inserted into the SmaI restriction enzyme cleavage site of pMW219, which is a plasmid vector for *E. coli* and unable to replicate in the *Bacillus subtilis* cell, to thereby construct plasmids pMWPHsigA and pMW-PFsigA employed in introducing, into the genome of *Bacillus subtilis*, the sigA gene containing the promoter transcribed specifically during the sporulation stage.

The above procedure was repeated, except that primers sigAmf and sigFUr-sigAm shown in Table 8 was employed instead of the primers sigAf and sigFUr-sigA, to thereby construct pMWPFsigAm in which an initiation codon (ATG) of the sigA gene in pMWPFsigA was substituted with a codon (ATA) which was not recognized as an initiation codon.

Example 2

Introduction of the sigA Gene Containing Promoter Transcribed Specifically During the Sporulation Stage into the Genome of *Bacillus subtilis* 168

*Bacillus subtilis* 168 was transformed through the competent method with the plasmid pMWPHsigA, pMWPFsigA, or pMWPFsigAm. The plasmids pMWPHsigA and pMW-PFsigA were employed for introducing, into the genome of *Bacillus subtilis*, the sigA gene containing the promoter transcribed specifically during the sporulation stage. The plasmid pMWPFsigAm was employed for introducing, into the genome of *Bacillus subtilis*, a modified sigA gene (sigAm) containing the same promoter, in which an initiation codon (ATG) of the sigA gene had been substituted by a codon (ATA). Colonies grown in an LB agar medium containing chloramphenicol were collected as transformants. Subsequently, the genome of the each transformant produced by use of pMWPHsigA or pMWPFsigA, serving as a template, was extracted, and PCR was performed thereon, to thereby confirm that the sigA gene containing the promoter transcribed specifically during the sporulation stage was inserted, together with the 1.2 kb fragment (D), into the genome through homologous recombination between the sigA gene of the genome and the sigA gene of pMWPHsigA or pMW-PFsigA. In a similar manner, the genome of the each transformant produced by use of pMWPFsigAm was employed as serving as a template, to thereby confirm that the sigAm was inserted, together with the 1.2 kb fragment (D), into the genome through homologous recombination between the sigA gene of the genome and the sigAm of pMWPFsigAm. The three transformants produced by use of pMWPHsigA, pMWPFsigA, and pMWPFsigAm, respectively, were denominated 168PHsigA, 168 PFsigA, and 168 PFsigAm.

Example 3

Evaluation of *Bacillus subtilis* Mutant Strain in Terms of Alkaline Cellulase Production (Secretion) Performance To each of the three types of *Bacillus subtilis* mutant strains obtained in Example 2 (168PHsigA, 168 PFsigA, and 168 PFsigAm) and to *Bacillus subtilis* 168 serving as a control, a recombinant plasmid pHY-S237 was introduced through the protoplast transformation method. The recombinant plasmid pHY-S237 was prepared by inserting a DNA fragment (3.1 kb) encoding an alkaline cellulase (JP-A-2000-210081) derived from *Bacillus* sp. KSM-S237 (FERM BP-7875) into the restriction enzyme BamHI cleavage site of a shuttle vector pHY300PLK (yakult). The cells were shake-cultured in LB medium (10 mL) overnight at 37° C. The culture broth (0.05 mL) was inoculated to a 2×L-maltose medium (50 mL) (2% tryptone, 1% yeast extract, 1% NaCl, 7.5% maltose, 7.5 ppm manganese sulfate 4-5 hydrate, and 15 ppm tetracycline), followed by shake-culturing at 30° C. for three days. After completion of culturing, cells were removed through centrifugation, and alkaline cellulase activity of the supernatant obtained from the culture was determined, thereby calculating the amount of the alkaline cellulase secreted from the cells during culturing; i.e., the amount of the extracellularly produced alkaline cellulase. As is clear from Table 9, more effective production, or secretion, of alkaline cellulase has been confirmed in the case where 168PHsigA or 168 PFsigA was employed as a host cell, as compared with the control strain 168 (wild type). Meanwhile, equivalent secretion of alkaline cellulase has been confirmed in the case where 168 PFsigAm was employed as a host cell, as compared with the control strain 168 (wild type). Thus, since the sigA gene, which was newly introduced into the genome, containing the promoter for expressing the sigH gene or the promoter for expressing the spoIIA operon was expressed to thereby produce SigA, more effective production may be attained in the case where 168PHsigA or 168 PFsigA was employed.

TABLE 8

| Primer | Nucleotide sequence | SEQ ID NO. |
| --- | --- | --- |
| SigAf | ATGGCTGATAAACAAACCCA | 8 |
| SigAr | CACCACAATGTTCATTTGCA | 9 |
| sigHuf | ACAGCCTTTCTTCCTCATTCT | 10 |
| sigHUr-sigA | CGTGGGTTTGTTTATCAGCCATTCCGATCCCCCCGGCGCACG | 11 |
| sigFUf | GCTGATAGAACGTGACACGGG | 12 |
| sigFUr-sigA | CGTGGGTTTGTTTATCAGCCATGCTCATTCCTCCTTGATATG | 13 |
| CmFW | CAACTAAAGCACCCATTAG | 14 |
| Cmr-sigA | CATTTGCAAATGAACATTGTGGTGCTTCTTCAACTAACGGGCA | 15 |
| sigAmf | ATAGCTGATAAACAAACCCA | 16 |
| sigFUr-sigAm | CGTGGGTTTGTTTATCAGCTATGCTCATTCCTCCTTGATATG | 17 |

TABLE 9

| Host | Amount of produced (secreted) alkaline cellulase (relative value) |
|---|---|
| 168 (wild type strain) | 100 |
| 168PHsigA | 135 |
| 168PFsigA | 146 |
| 168PFsigAm | 108 |

Example 4

Evaluation of *Bacillus subtilis* Mutant Strain in Terms of Alkaline Protease Production (Secretion) Performance 168PHsigA and 168 PFsigA, exhibiting enhanced alkaline cellulase productivity confirmed in Example 3, were evaluated in terms of production performance of other proteins and polypeptides. Specifically, among others, alkaline protease production performance of the above two strains was investigated by use of the genus *Bacillus* in the following procedure.

A genome DNA sample, serving as a template, extracted from *Bacillus clausii* KSM-K16 (FERM BP-3376) and a primer set of S237pKAPpp-F and KAPter-R (BglII) shown in Table 10 were employed, to thereby amplify through PCR a 1.3 kb DNA fragment (G) encoding alkaline protease (Appl. Microbiol. Biotechnol., 43, 473, (1995)) having an amino acid sequence represented by SEQ ID NO: 21. Separately, a genome DNA sample, serving as a template, extracted from *Bacillus* sp. KSM-S237 (FERM BP-7875) and a primer set of S237ppp-F2 (BamHI) and S237pKAPpp-R shown in Table 10 were employed, to thereby amplify through PCR a 0.6 kb DNA fragment (H) containing a promoter region of an alkaline cellulase gene (JP-A-2000-210081). Subsequently, SOE-PCR was performed by use of a primer set of S237 ppp-F2 (BamHI) and KAPter-R (BglII) shown in Table 10 and the thus-obtained two fragments (G) and (H) in combination as templates, to thereby produce a 1.8 kb DNA fragment (I) in which an alkaline protease gene was ligated to downstream of the promoter region of an alkaline cellulase gene. The thus-produced 1.8 kb DNA fragment (I) was inserted into the BamHI-BglII restriction enzyme cleavage site of a shuttle vector pHY300PLK (yakult), to thereby construct a plasmid pHYKAP (S237p) for evaluating alkaline protease productivity.

The thus-constructed plasmid pHYKAP (S237p) was introduced to each of the 168PHsigA and 168 PFsigA, and to *Bacillus subtilis* 168 serving as a control through the protoplast transformation method. The cells were shake-cultured for three days, and other conditions were the same as employed in Example 3. After completion of culturing, cells were removed through centrifugation, and alkaline protease activity of the supernatant obtained from the culture was determined, thereby calculating the amount of the alkaline protease secreted from the cells during culturing; i.e., the amount of the extracellularly produced alkaline protease. As is clear from Table 11, more effective production, or secretion, of alkaline protease has been confirmed in the case where 168PHsigA or 168 PFsigA was employed as a host cell, as compared with the control 168 strain (wild type).

TABLE 10

| Primer | Nucleotide sequence | SEQ ID NO. |
|---|---|---|
| S237pKAPpp-F | ACTTTAAAAATATTTAGGAGGTAATATGAAGAAACCGTTGGGGAA | 22 |
| KAPter-R (BglII) | GGGAGATCTTCAGCGATCTATTTCTCTTTTTC | 23 |
| S237ppp-F2 (BamHI) | CCCGGATCCAACAGGCTTATATTTA | 24 |
| S237pKAPpp-R | TTTCCCCAACGGTTTCTTCATATTACCTCCTAAATATTTTTAAAGT | 25 |
| K38matu-F2 (ALAA) | GCTCTTGCAGCAGATGGATTGAACGGTACG | 26 |
| SP64K38-R (XbaI) | TTGGTCTAGACCCCAAGCTTCAAAGTCGTA | 27 |
| S237ppp-R2 (ALAA) | TTCAATCCATCTGCTGCAAGAGCTGCCGG | 28 |

TABLE 11

| Host | Amount of produced (secreted) alkaline protease (relative value) |
|---|---|
| 168 (wild type strain) | 100 |
| 168PHsigA | 129 |
| 168PFsigA | 130 |

Example 5

Evaluation of *Bacillus subtilis* Mutant Strain in Terms of Alkaline Amylase Production (Secretion) Performance 168PHsigA and 168 PFsigA, exhibiting enhanced alkaline cellulase and alkaline protease productivities confirmed in Examples 3 and 4, were evaluated in terms of production performance of other proteins and polypeptides. Specifically, among others, alkaline amylase production performance of the above two strains was investigated by use of the genus *Bacillus* in the following procedure.

A genome DNA sample, serving as a template, extracted from *Bacillus* sp. KSM-K38 (FERM BP-6946) and a primer set of K38matu-F2 (ALAA) and SP64K38-R (XbaI) shown in Table 10 were employed, to thereby amplify through PCR a 1.5 kb DNA fragment (J) encoding alkaline amylase (Appl. Environ. Microbiol., 67, 1744, (2001)) having an amino acid sequence represented by SEQ ID NO: 19. Separately, a genome DNA sample, serving as a template, extracted from *Bacillus* sp. KSM-S237 (FERM BP-7875) and a primer set of S237 ppp-F2 (BamHI) and S237 ppp-R2 (ALAA) shown in Table 10 were employed, to thereby amplify through PCR a 0.6 kb DNA fragment (K) containing a promoter region of an alkaline cellulase gene (JP-A-2000-210081) and a region encoding a secretory signal sequence. Subsequently, SOE-PCR was performed by use of a primer set of S237 ppp-F2 (BamHI) and SP64K38-R (XbaI) shown in Table 10 and the thus-obtained two fragments (J) and (K) in combination as templates, to thereby produce a 2.1 kb DNA fragment (L) in which an alkaline amylase gene was ligated downstream of the promoter region of an alkaline cellulase gene and the region encoding a secretory signal sequence. The thus-produced 2.2 kb DNA fragment (L) was inserted into the BamHI-XbaI restriction enzyme cleavage site of a shuttle vector pHY300PLK (yakult), to thereby construct a plasmid pHYK38 (S237ps) for evaluating alkaline amylase productivity.

The thus-constructed plasmid pHYK38 (S237ps) was introduced to each of the 168PHsigA and 168 PFsigA, and to *Bacillus subtilis* 168 serving as a control through the protoplast transformation method. The cells were shake-cultured for five days, and other conditions were the same as employed in Example 3. After completion of culturing, cells were removed through centrifugation, and alkaline amylase activity of the supernatant obtained from the culture was determined, thereby calculating the amount of the amylase secreted from the cells during culturing; i.e., the amount of the extracellularly produced amylase. As is clear from Table 12, more effective production, or secretion, of alkaline amylase has been confirmed in the case where 168PHsigA or 168 PFsigA was employed as a host cell, as compared with the control strain 168 (wild type). Thus, it was revealed that the aforementioned mutant strains were employed effectively in producing a variety of proteins and polypeptides.

TABLE 12

| Host | Amount of produced (secreted) alkaline amylase (relative value) |
| --- | --- |
| 168 (wild type strain) | 100 |
| 168PHsigA | 189 |
| 168PFsigA | 182 |

The invention claimed is:

1. An isolated or purified *Bacillus* bacterium comprising:
   a polynucleotide promoter sequence recognized and transcribed specifically during a sporulation stage, and
   a polynucleotide that encodes a SigA polypeptide having the amino acid sequence of SEQ ID NO: 1 or a polypeptide that is at least 80% homologous to the amino acid sequence of SEQ ID NO: 1 and which participates in transcription of a gene which is essential for growth during the vegetative growth period of said *Bacillus* bacterium,
   wherein the promoter sequence is located between 1 to 198 bp upstream of, and operatively-linked to, said polynucleotide encoding sigA; and wherein the promoter sequence is selected from the group consisting of a promoter sequence for expressing sigH gene of *Bacillus* and a promoter sequence for expressing spoIIA operon of *Bacillus*.

2. The isolated or purified *Bacillus* bacterium, wherein the promoter sequence is selected from the group consisting of a promoter sequence for expressing sigH gene of *Bacillus* that contains the nucleotide sequence from base numbers 987 to 1,027 of SEQ ID NO: 2, and a promoter sequence for expressing spoIIA operon of *Bacillus* that contains a nucleotide sequence from base numbers 1,081 to 1,110 of SEQ ID NO: 3.

3. The isolated or purified *Bacillus* bacterium of claim 1 which is *Bacillus subtilis*.

4. The isolated or purified *Bacillus* bacterium of claim 1, further comprising a heterologous polynucleotide encoding a protein or polypeptide.

5. A method for producing a protein or a polypeptide comprising expressing a heterologous polynucleotide in the *Bacillus* bacterium of claim 4, and
recovering said protein or polypeptide.

6. The method of claim 5, wherein the protein or polypeptide is a cellulase, amylase, or protease.

7. The method of claim 5, wherein the protein or polypeptide comprises an amino acid sequence that is at least 70% homologous to SEQ ID NO: 4.

8. The method of claim 5, wherein the protein or polypeptide comprises an amino acid sequence that is at least 70% homologous to SEQ ID NO: 19.

9. The method of claim 5, wherein the protein or polypeptide comprises an amino acid sequence that is at least 70% homologous to SEQ ID NO: 21.

10. A method for constructing the *Bacillus* bacterium of claim 1 comprising:
transforming a *Bacillus* bacterium with a polynucleotide comprising a promoter sequence recognized and transcribed specifically during a sporulation stage, a polynucleotide that encodes a SigA polypeptide having the amino acid sequence of SEQ ID NO: 1 or a polypeptide that is at least 80% homologous to the amino acid sequence of SEQ ID NO: 1 and which participates in transcription of a gene which is essential for growth during the vegetative growth period of said *Bacillus* bacterium,
wherein the promoter sequence is located between 1 to 198 by upstream of, and operatively-linked to, said polynucleotide encoding sigA; and wherein the promoter sequence is selected from the group consisting of a promoter sequence for expressing sigH gene of *Bacillus* that contains the nucleotide sequence from base numbers 987 to 1,027 of SEQ ID NO: 2, and a promoter sequence for expressing spoIIA operon of *Bacillus* that contains a nucleotide sequence from base numbers 1,081 to 1,110 of SEQ ID NO: 3.

11. The method of claim 10, wherein said promoter sequence is one for expressing sigH gene of *Bacillus* that contains the nucleotide sequence from base numbers 987 to 1,027 of SEQ ID NO: 2.

12. The method of claim 10, wherein said promoter sequence is one for expressing spoIIA operon of *Bacillus* that contains a nucleotide sequence from base numbers 1,081 to 1,110 of SEQ ID NO: 3.

13. The method of claim 10, wherein said sigA gene encodes the polypeptide comprising SEQ ID NO: 1.

14. The isolated or purified *Bacillus* bacterium of claim 1, which has the promoter sequence and the polynucleotide encoding SigA protein integrated into its genomic DNA.

15. The isolated or purified *Bacillus* bacterium of claim 1, wherein said *Bacillus* has the promoter sequence and the polynucleotide encoding SigA protein located on a plasmid.

16. The isolated or purified *Bacillus* bacterium of claim 1, wherein said sigA gene encodes the polypeptide comprising SEQ ID NO: 1.

17. The isolated or purified *Bacillus* bacterium of claim 1, further comprising a heterologous polynucleotide encoding a protein or polypeptide.

18. The isolated or purified *Bacillus* bacterium of claim 1, further comprising a heterologous polynucleotide encoding a protein or polypeptide that is at least 70% homologous to the amino acid sequence of SEQ ID NO: 4.

19. The isolated or purified *Bacillus* bacterium of claim 1, further comprising a heterologous polynucleotide encoding a protein or polypeptide that is at least 70% homologous to the amino acid sequence of SEQ ID NO: 19.

20. The isolated or purified *Bacillus* bacterium of claim 1, further comprising a heterologous polynucleotide encoding a protein or polypeptide that is at least 70% homologous to the amino acid sequence of SEQ ID NO: 21.

* * * * *